(12) United States Patent
Lofthouse et al.

(10) Patent No.: US 8,696,719 B2
(45) Date of Patent: Apr. 15, 2014

(54) METHODS AND DEVICES FOR TREATING HALLUX VALGUS

(75) Inventors: Trevor Lofthouse, Sunnyvale, CA (US); Paul M. Sand, Redwood City, CA (US); Nick Mourlas, Mountain View, CA (US); John Avi Roop, John, CA (US)

(73) Assignee: Tarsus Medical Inc., Mountain View, CA (US)

( * ) Notice: Subject to any disclaimer, the term of this patent is extended or adjusted under 35 U.S.C. 154(b) by 375 days.

(21) Appl. No.: 12/793,429

(22) Filed: Jun. 3, 2010

(65) Prior Publication Data
US 2011/0301648 A1 Dec. 8, 2011

(51) Int. Cl.
*A61B 17/58* (2006.01)

(52) U.S. Cl.
USPC .............................. 606/313; 606/104; 606/305

(58) Field of Classification Search
USPC .................... 411/43; 606/104, 232, 300–301, 606/313–314, 318–320, 304–310, 606/323–328; 623/13.13–13.16
See application file for complete search history.

(56) References Cited

U.S. PATENT DOCUMENTS

| | | |
|---|---|---|
| 2,291,413 A | 7/1942 | Sand |
| 3,867,929 A | 2/1975 | Joyner et al. |
| 3,880,155 A | 4/1975 | Rosoff |
| 3,987,559 A | 10/1976 | Roberts |
| 4,069,824 A | 1/1978 | Weinstock |
| 4,213,208 A | 7/1980 | Marne |
| 4,240,214 A | 12/1980 | Sigle et al. |
| 4,244,359 A | 1/1981 | Dieterich |
| 4,255,875 A | 3/1981 | Gilkerson |
| 4,263,902 A | 4/1981 | Dieterich |
| 4,266,553 A | 5/1981 | Faiella |
| 4,300,294 A | 11/1981 | Riecken |
| 4,314,412 A | 2/1982 | Anderson et al. |
| 4,317,293 A | 3/1982 | Sigle et al. |
| 4,393,876 A | 7/1983 | Dieterich |
| 4,409,974 A | 10/1983 | Freedland |
| 4,414,964 A | 11/1983 | Farino et al. |
| 4,439,934 A | 4/1984 | Brown |
| 4,497,603 A | 2/1985 | Boucher et al. |
| 4,510,699 A | 4/1985 | Nakamura et al. |
| 4,583,303 A | 4/1986 | Laiacona et al. |
| 4,597,195 A | 7/1986 | Dananberg |

(Continued)

FOREIGN PATENT DOCUMENTS

| | | | |
|---|---|---|---|
| EP | 40782 | A2 | 12/1981 |
| EP | 60353 | A1 | 9/1982 |

(Continued)

OTHER PUBLICATIONS

Mini TightRope™ for Hallux Valgus Correction and Lisfranc Ligament Repair Surgical Technique, Anthrex, copyright 2007, 6 pp. H. Kelikian, M.D., "Miscellaneous Methods", Hallux Valgus, Allied Deformities of the Forefoot and Metatarsalgia, 1965, pp. 253-261, W.B. Saunders Company, Philadelphia and London.

(Continued)

*Primary Examiner* — Nicholas Woodall
*Assistant Examiner* — Larry E Waggle, Jr.
(74) *Attorney, Agent, or Firm* — Peter Materna; Eva Tan

(57) ABSTRACT

The various embodiments disclosed herein relate to implantable devices for the treatment of structural bone and joint deformity, including hallux valgus. More specifically, the various embodiments include systems, devices, and methods for implantation of an implantable device having at least one bone anchor with deployable prongs for treating such deformity.

25 Claims, 16 Drawing Sheets

(56) References Cited

U.S. PATENT DOCUMENTS

| | | |
|---|---|---|
| 4,603,698 A | 8/1986 | Guttmann Cherniak |
| 4,604,997 A | 8/1986 | De Bastiani et al. |
| 4,608,988 A | 9/1986 | Dananberg |
| 4,620,825 A | 11/1986 | Potzas |
| 4,632,103 A | 12/1986 | Fabricant et al. |
| 4,644,940 A | 2/1987 | Nakamura |
| 4,676,801 A | 6/1987 | Lundeen |
| 4,726,127 A | 2/1988 | Barouk |
| 4,729,369 A | 3/1988 | Cook |
| 4,738,255 A | 4/1988 | Goble et al. |
| RE32,698 E | 6/1988 | Brown |
| 4,772,286 A * | 9/1988 | Goble et al. ............... 623/13.14 |
| 4,813,162 A | 3/1989 | Harris |
| 4,819,644 A | 4/1989 | Cherniak |
| 4,841,647 A | 6/1989 | Turucz |
| 4,842,931 A | 6/1989 | Zook |
| 4,852,556 A | 8/1989 | Groiso |
| 4,856,505 A | 8/1989 | Shaffer et al. |
| 4,859,128 A | 8/1989 | Brecz et al. |
| 4,876,758 A | 10/1989 | Rolloff et al. |
| 4,901,453 A | 2/1990 | Gaynor |
| 4,930,504 A | 6/1990 | Diamantopoulos et al. |
| 4,940,046 A | 7/1990 | Jacoby |
| 4,969,277 A | 11/1990 | Williams |
| 4,976,712 A | 12/1990 | VanderSlik |
| 5,005,575 A | 4/1991 | Geri |
| 5,012,596 A | 5/1991 | Schiller |
| 5,035,069 A | 7/1991 | Minden |
| 5,044,850 A | 9/1991 | Getten et al. |
| 5,092,347 A | 3/1992 | Shaffer et al. |
| 5,094,226 A | 3/1992 | Medcalf et al. |
| 5,098,421 A | 3/1992 | Zook |
| 5,138,777 A | 8/1992 | Darby |
| 5,167,665 A | 12/1992 | McKinney |
| 5,174,052 A | 12/1992 | Schoenhaus et al. |
| 5,250,049 A | 10/1993 | Michael |
| D341,424 S | 11/1993 | Lurie |
| 5,272,139 A | 12/1993 | Cary, Jr. |
| 5,306,301 A | 4/1994 | Graf et al. |
| 5,350,383 A | 9/1994 | Schmieding et al. |
| RE34,753 E | 10/1994 | Groiso |
| 5,497,789 A | 3/1996 | Zook |
| 5,503,510 A | 4/1996 | Golan |
| 5,529,075 A | 6/1996 | Clark |
| 5,537,764 A | 7/1996 | Prahl |
| 5,539,020 A | 7/1996 | Bracken et al. |
| 5,571,139 A | 11/1996 | Jenkins, Jr. |
| 5,601,565 A | 2/1997 | Huebner |
| 5,607,756 A | 3/1997 | Yamauchi et al. |
| 5,611,801 A | 3/1997 | Songer |
| 5,617,651 A | 4/1997 | Prahl |
| 5,618,142 A | 4/1997 | Sonden et al. |
| 5,640,779 A | 6/1997 | Rolloff et al. |
| 5,645,588 A | 7/1997 | Graf et al. |
| 5,665,060 A | 9/1997 | Fabricant |
| 5,665,112 A | 9/1997 | Thal |
| 5,685,834 A | 11/1997 | Barth |
| H1706 H | 1/1998 | Mason |
| 5,713,903 A | 2/1998 | Sander et al. |
| 5,725,541 A | 3/1998 | Anspach, III et al. |
| 5,725,585 A | 3/1998 | Zobel |
| 5,728,136 A | 3/1998 | Thal |
| 5,788,697 A | 8/1998 | Kilpela et al. |
| 5,792,093 A | 8/1998 | Tanaka |
| 5,797,913 A | 8/1998 | Dambreville et al. |
| 5,802,737 A | 9/1998 | Beppu |
| 5,810,822 A | 9/1998 | Mortier |
| 5,843,085 A | 12/1998 | Graser |
| 5,853,293 A | 12/1998 | Weber et al. |
| 5,919,194 A | 7/1999 | Anderson |
| 5,921,986 A | 7/1999 | Bonutti |
| 5,962,011 A | 10/1999 | DeVillez et al. |
| 6,001,101 A | 12/1999 | Augagneur et al. |
| 6,068,648 A | 5/2000 | Cole et al. |
| 6,091,000 A | 7/2000 | Haynes |
| 6,093,163 A | 7/2000 | Chong et al. |
| 6,203,545 B1 | 3/2001 | Stoffella |
| 6,238,357 B1 | 5/2001 | Kawaguchi et al. |
| D443,694 S | 6/2001 | Ford |
| 6,248,109 B1 | 6/2001 | Stoffella |
| 6,248,788 B1 | 6/2001 | Robbins et al. |
| 6,264,677 B1 | 7/2001 | Simon et al. |
| 6,283,973 B1 | 9/2001 | Hubbard et al. |
| 6,299,398 B1 | 10/2001 | Shinjo |
| 6,315,749 B1 | 11/2001 | Sunayama |
| 6,318,373 B1 | 11/2001 | Kasahara |
| 6,319,270 B1 | 11/2001 | Grafton et al. |
| 6,348,053 B1 | 2/2002 | Cachia |
| 6,367,087 B1 | 4/2002 | Spillman et al. |
| 6,391,031 B1 | 5/2002 | Toomey |
| 6,406,234 B2 | 6/2002 | Frigg |
| 6,424,864 B1 | 7/2002 | Matsuura |
| 6,447,783 B1 | 9/2002 | Yayon |
| 6,478,761 B2 | 11/2002 | Bracamonte-Sommer |
| 6,481,120 B1 | 11/2002 | Xia et al. |
| 6,514,222 B2 | 2/2003 | Cook |
| 6,547,792 B1 | 4/2003 | Tsuji et al. |
| 6,547,800 B2 | 4/2003 | Foerster et al. |
| 6,569,188 B2 | 5/2003 | Grafton et al. |
| 6,583,114 B2 | 6/2003 | Vickery |
| 6,604,301 B1 | 8/2003 | Manoli, II et al. |
| 6,616,665 B2 | 9/2003 | Grafton et al. |
| 6,629,943 B1 | 10/2003 | Schroder |
| 6,643,956 B2 | 11/2003 | Mawusi et al. |
| 6,684,532 B2 | 2/2004 | Greene et al. |
| 6,689,136 B2 | 2/2004 | Stoffella |
| 6,716,234 B2 | 4/2004 | Grafton et al. |
| 6,749,384 B1 | 6/2004 | Ellis |
| 6,800,063 B2 | 10/2004 | Iwata |
| 6,862,481 B1 | 3/2005 | Demian |
| 6,874,258 B2 | 4/2005 | Clough et al. |
| 6,887,243 B2 | 5/2005 | Culbert |
| 6,887,259 B2 | 5/2005 | Lizardi |
| 6,889,088 B2 | 5/2005 | Demian |
| 6,890,333 B2 | 5/2005 | von Hoffmann et al. |
| 6,902,799 B2 | 6/2005 | Chikamori |
| 6,905,296 B2 | 6/2005 | Millington |
| 6,908,465 B2 | 6/2005 | von Hoffmann et al. |
| 6,909,513 B2 | 6/2005 | Fujita et al. |
| 6,910,287 B2 | 6/2005 | Truelsen |
| 6,942,668 B2 | 9/2005 | Padget et al. |
| 6,964,645 B1 | 11/2005 | Smits |
| 6,991,636 B2 | 1/2006 | Rose |
| 7,008,428 B2 | 3/2006 | Cachia et al. |
| 7,013,583 B2 | 3/2006 | Greene et al. |
| 7,052,498 B2 | 5/2006 | Levy et al. |
| 7,055,268 B2 | 6/2006 | Ha |
| 7,056,885 B1 | 6/2006 | Jeffers et al. |
| 7,062,866 B2 | 6/2006 | Bussler |
| 7,070,601 B2 | 7/2006 | Culbert et al. |
| 7,097,647 B2 | 8/2006 | Segler |
| 7,141,545 B2 | 11/2006 | Pike et al. |
| 7,175,667 B2 | 2/2007 | Saunders et al. |
| 7,182,561 B2 | 2/2007 | Jones |
| 7,192,411 B2 | 3/2007 | Gobet et al. |
| 7,217,853 B2 | 5/2007 | Kulichikhin et al. |
| 7,253,266 B2 | 8/2007 | Shimkets et al. |
| 7,263,788 B2 | 9/2007 | Johnson |
| 7,266,910 B2 | 9/2007 | Ingimundarson |
| 7,270,644 B2 | 9/2007 | Ingimundarson |
| 7,273,338 B2 | 9/2007 | Summerlin |
| 7,276,244 B2 | 10/2007 | Radovic |
| 7,287,293 B2 | 10/2007 | Cook et al. |
| 7,291,175 B1 | 11/2007 | Gordon |
| 7,291,483 B2 | 11/2007 | Shimkets et al. |
| 7,322,783 B2 | 1/2008 | Pearce et al. |
| 7,325,323 B2 | 2/2008 | Katsu et al. |
| 7,326,211 B2 | 2/2008 | Padget et al. |
| 7,383,089 B2 | 6/2008 | Demian |
| 7,384,226 B2 | 6/2008 | Jones et al. |
| 7,392,605 B2 | 7/2008 | Hatfield et al. |
| 7,396,338 B2 | 7/2008 | Huber et al. |
| 7,485,135 B2 * | 2/2009 | Steiger et al. ............... 606/300 |
| 7,485,153 B2 | 2/2009 | Padmanabhan et al. |

(56) References Cited

U.S. PATENT DOCUMENTS

| | | |
|---|---|---|
| 7,493,810 B2 | 2/2009 | Walczyk et al. |
| 7,513,880 B2 | 4/2009 | Ingimundarson et al. |
| 7,572,258 B2 | 8/2009 | Stiernborg |
| 7,625,395 B2 | 12/2009 | Muckter |
| 7,650,681 B2 | 1/2010 | Jones et al. |
| 7,722,303 B2 | 5/2010 | Williams |
| 7,824,141 B2 | 11/2010 | Jones et al. |
| 7,833,255 B2 | 11/2010 | Chow et al. |
| 7,875,058 B2 | 1/2011 | Holmes, Jr. |
| 8,048,134 B2 * | 11/2011 | Partin ........................... 606/320 |
| 8,096,742 B2 | 1/2012 | Davies et al. |
| 2001/0027583 A1 | 10/2001 | Rothbart |
| 2001/0034956 A1 | 11/2001 | Mawusi et al. |
| 2002/0007134 A1 | 1/2002 | Bracamonte-Sommer |
| 2002/0022862 A1 | 2/2002 | Grafton et al. |
| 2002/0032466 A1 | 3/2002 | Grafton et al. |
| 2002/0056209 A1 | 5/2002 | Clough et al. |
| 2002/0058036 A1 | 5/2002 | Jeffers et al. |
| 2002/0062140 A1 | 5/2002 | Demian |
| 2002/0077281 A1 | 6/2002 | Vickery |
| 2002/0138026 A1 | 9/2002 | Cook |
| 2002/0162250 A1 | 11/2002 | Campbell et al. |
| 2002/0193309 A1 | 12/2002 | Yayon |
| 2003/0005601 A1 | 1/2003 | Kasahara |
| 2003/0023268 A1 | 1/2003 | Lizardi |
| 2003/0040750 A1 | 2/2003 | Stoffella |
| 2003/0045881 A1 | 3/2003 | Barouk et al. |
| 2003/0093920 A1 | 5/2003 | Greene et al. |
| 2003/0105193 A1 | 6/2003 | Wang |
| 2003/0134792 A1 | 7/2003 | Pike et al. |
| 2003/0148692 A1 | 8/2003 | Chikamori |
| 2003/0152637 A1 | 8/2003 | Chasin et al. |
| 2003/0172553 A1 | 9/2003 | Truelsen |
| 2003/0186433 A1 | 10/2003 | Shimkets et al. |
| 2003/0187372 A1 | 10/2003 | Iwata |
| 2003/0225356 A1 | 12/2003 | Kulichikhin et al. |
| 2004/0019308 A1 | 1/2004 | Chow |
| 2004/0031169 A1 | 2/2004 | Jensen et al. |
| 2004/0039319 A1 | 2/2004 | Calatayud Carral |
| 2004/0045194 A1 | 3/2004 | Kumai |
| 2004/0071522 A1 | 4/2004 | Millington |
| 2004/0093746 A1 | 5/2004 | Varsallona |
| 2004/0103561 A1 | 6/2004 | Campbell et al. |
| 2004/0107604 A1 | 6/2004 | Ha |
| 2004/0123495 A1 | 7/2004 | Greene et al. |
| 2004/0127907 A1 | 7/2004 | Dakin et al. |
| 2004/0153153 A1 * | 8/2004 | Elson et al. ................ 623/13.14 |
| 2004/0156931 A1 | 8/2004 | Burch et al. |
| 2004/0161481 A1 | 8/2004 | Burch et al. |
| 2004/0168329 A1 | 9/2004 | Ishimaru |
| 2004/0168353 A1 | 9/2004 | Bussler |
| 2004/0186182 A1 | 9/2004 | Burch et al. |
| 2004/0191338 A1 | 9/2004 | Burch et al. |
| 2004/0194348 A1 | 10/2004 | Campbell et al. |
| 2004/0194352 A1 | 10/2004 | Campbell et al. |
| 2004/0210234 A1 | 10/2004 | Coillard et al. |
| 2004/0243197 A1 | 12/2004 | Demian |
| 2005/0019436 A1 | 1/2005 | Burch et al. |
| 2005/0020690 A1 | 1/2005 | Burch et al. |
| 2005/0054959 A1 | 3/2005 | Ingimundarson |
| 2005/0054962 A1 | 3/2005 | Bradshaw |
| 2005/0055849 A1 | 3/2005 | Ha |
| 2005/0058734 A1 | 3/2005 | Burch et al. |
| 2005/0059873 A1 | 3/2005 | Glozman et al. |
| 2005/0060910 A1 | 3/2005 | Kaneda et al. |
| 2005/0061332 A1 | 3/2005 | Greenawalt et al. |
| 2005/0063971 A1 | 3/2005 | Jeffers et al. |
| 2005/0070909 A1 | 3/2005 | Egger et al. |
| 2005/0076536 A1 | 4/2005 | Hatfield et al. |
| 2005/0115116 A1 | 6/2005 | Pedersen et al. |
| 2005/0123567 A1 | 6/2005 | First |
| 2005/0158382 A1 | 7/2005 | Cruz et al. |
| 2005/0177084 A1 | 8/2005 | Green et al. |
| 2005/0187071 A1 | 8/2005 | Yamashita et al. |
| 2005/0197711 A1 | 9/2005 | Cachia |
| 2005/0202047 A1 | 9/2005 | Radovic |
| 2005/0208540 A1 | 9/2005 | Shimkets et al. |
| 2005/0228389 A1 | 10/2005 | Stiernborg |
| 2005/0229430 A1 | 10/2005 | Takaba |
| 2005/0229433 A1 | 10/2005 | Cachia |
| 2005/0241187 A1 | 11/2005 | Johnson |
| 2005/0251081 A1 | 11/2005 | McClanahan et al. |
| 2006/0002954 A1 | 1/2006 | Tabata et al. |
| 2006/0015102 A1 | 1/2006 | Toullec et al. |
| 2006/0030854 A1 | 2/2006 | Haines |
| 2006/0058796 A1 | 3/2006 | Hartdegen et al. |
| 2006/0064048 A1 | 3/2006 | Stano |
| 2006/0074434 A1 | 4/2006 | Wenstrom et al. |
| 2006/0079558 A1 | 4/2006 | Aberg et al. |
| 2006/0079559 A1 | 4/2006 | Aberg et al. |
| 2006/0081553 A1 | 4/2006 | Patterson et al. |
| 2006/0148903 A1 | 7/2006 | Burch et al. |
| 2006/0155233 A1 | 7/2006 | Huber et al. |
| 2006/0161090 A1 | 7/2006 | Lee |
| 2006/0162464 A1 | 7/2006 | Hayashi et al. |
| 2006/0178702 A1 | 8/2006 | Pierce et al. |
| 2006/0189914 A1 | 8/2006 | Slavitt |
| 2006/0201011 A1 | 9/2006 | Katsu et al. |
| 2006/0240105 A1 | 10/2006 | Devane et al. |
| 2006/0241066 A1 | 10/2006 | Tomita et al. |
| 2006/0241607 A1 | 10/2006 | Myerson et al. |
| 2006/0241608 A1 | 10/2006 | Myerson et al. |
| 2006/0247566 A1 | 11/2006 | Gobet et al. |
| 2006/0251721 A1 | 11/2006 | Cruz et al. |
| 2006/0258588 A1 | 11/2006 | Pike et al. |
| 2006/0264961 A1 | 11/2006 | Murray-Brown |
| 2006/0269628 A1 | 11/2006 | Burch et al. |
| 2006/0271077 A1 | 11/2006 | Graser |
| 2006/0276737 A1 | 12/2006 | Rose |
| 2006/0282231 A1 | 12/2006 | Kurashina et al. |
| 2007/0010818 A1 | 1/2007 | Stone et al. |
| 2007/0016205 A1 | 1/2007 | Beutter et al. |
| 2007/0016275 A1 | 1/2007 | Ferdinand |
| 2007/0033750 A1 | 2/2007 | Cook et al. |
| 2007/0036876 A1 | 2/2007 | Burch et al. |
| 2007/0051020 A1 | 3/2007 | Tajima et al. |
| 2007/0051376 A1 | 3/2007 | Kulichikhin et al. |
| 2007/0074334 A1 | 4/2007 | Steel |
| 2007/0074426 A1 | 4/2007 | Dorsey |
| 2007/0078518 A1 | 4/2007 | Lavi |
| 2007/0088341 A1 | 4/2007 | Skiba et al. |
| 2007/0094896 A1 | 5/2007 | Hatfield et al. |
| 2007/0128226 A1 | 6/2007 | Radovic |
| 2007/0131798 A1 | 6/2007 | Katsukawa et al. |
| 2007/0141020 A1 | 6/2007 | Barritault et al. |
| 2007/0197948 A1 | 8/2007 | Ingimundarson et al. |
| 2007/0204487 A1 | 9/2007 | Clough |
| 2007/0213296 A1 | 9/2007 | Zhang |
| 2007/0213308 A1 | 9/2007 | Lessem et al. |
| 2007/0214681 A1 | 9/2007 | Dezfouli |
| 2007/0225217 A1 | 9/2007 | Chappell et al. |
| 2007/0225703 A1 | 9/2007 | Schmitz et al. |
| 2007/0260252 A1 | 11/2007 | Schmitz et al. |
| 2007/0265296 A1 | 11/2007 | Dalton et al. |
| 2007/0265634 A1 | 11/2007 | Weinstein |
| 2007/0281906 A1 | 12/2007 | Dalton et al. |
| 2007/0282342 A1 | 12/2007 | Niederberger et al. |
| 2007/0299382 A1 | 12/2007 | Millet |
| 2008/0008777 A1 | 1/2008 | Radovic |
| 2008/0010856 A1 | 1/2008 | Hakkala |
| 2008/0014272 A1 | 1/2008 | Skolnick et al. |
| 2008/0027119 A1 | 1/2008 | Lippa et al. |
| 2008/0041169 A1 | 2/2008 | Walczyk et al. |
| 2008/0057068 A1 | 3/2008 | Dalton et al. |
| 2008/0065224 A1 | 3/2008 | Reigstad et al. |
| 2008/0076829 A1 | 3/2008 | Dalton et al. |
| 2008/0078628 A1 | 4/2008 | Christen |
| 2008/0081834 A1 | 4/2008 | Lippa et al. |
| 2008/0086139 A1 | 4/2008 | Bourke et al. |
| 2008/0086909 A1 | 4/2008 | Raspini |
| 2008/0086913 A1 | 4/2008 | Nawachi et al. |
| 2008/0102121 A1 | 5/2008 | Devane et al. |
| 2008/0113025 A1 | 5/2008 | Devane et al. |
| 2008/0139641 A1 | 6/2008 | Meyer |

(56) References Cited

U.S. PATENT DOCUMENTS

| | | |
|---|---|---|
| 2008/0141565 A1 | 6/2008 | Rini et al. |
| 2008/0147084 A1 | 6/2008 | Bleich et al. |
| 2008/0153780 A1 | 6/2008 | Meyer |
| 2008/0155731 A1 | 7/2008 | Kasahara |
| 2008/0200989 A1 | 8/2008 | Cachia |
| 2008/0208252 A1 | 8/2008 | Holmes |
| 2008/0216593 A1 | 9/2008 | Jacobsen et al. |
| 2008/0217816 A1 | 9/2008 | Hemmi et al. |
| 2008/0221697 A1 | 9/2008 | Graser |
| 2008/0229482 A1 | 9/2008 | Millet |
| 2008/0242646 A1 | 10/2008 | Lessem et al. |
| 2008/0248282 A1 | 10/2008 | Martin et al. |
| 2008/0260791 A1 | 10/2008 | Burch et al. |
| 2008/0262091 A1 | 10/2008 | Burch et al. |
| 2008/0263900 A1 | 10/2008 | Determe et al. |
| 2008/0280975 A1 | 11/2008 | Badul |
| 2008/0282580 A1 | 11/2008 | Ji-Woog |
| 2008/0287406 A1 | 11/2008 | Lessem |
| 2008/0287866 A1 | 11/2008 | Heller |
| 2008/0288019 A1 | 11/2008 | Heller |
| 2008/0294170 A1 | 11/2008 | O'Brien |
| 2008/0301977 A1 | 12/2008 | Roberts et al. |
| 2009/0005358 A1 | 1/2009 | Lessem |
| 2009/0012180 A1 | 1/2009 | Lange et al. |
| 2009/0036893 A1 | 2/2009 | Kartalian et al. |
| 2009/0043318 A1 | 2/2009 | Michel et al. |
| 2009/0054527 A1 | 2/2009 | Burch et al. |
| 2009/0062253 A1 | 3/2009 | Gahman et al. |
| 2009/0062359 A1 | 3/2009 | Burch et al. |
| 2009/0082466 A1 | 3/2009 | Babul |
| 2009/0082773 A1 | 3/2009 | Haines |
| 2009/0082874 A1 | 3/2009 | Cachia |
| 2009/0111792 A1 | 4/2009 | Burch et al. |
| 2009/0113759 A1 | 5/2009 | Heid |
| 2009/0117167 A1 | 5/2009 | Burch et al. |
| 2009/0118242 A1 | 5/2009 | Burch et al. |
| 2009/0133289 A1 | 5/2009 | Cantoni |
| 2009/0155614 A1 | 6/2009 | McLeod et al. |
| 2009/0157194 A1 | 6/2009 | Shikinami |
| 2009/0181098 A1 | 7/2009 | Garrett et al. |
| 2009/0192222 A1 | 7/2009 | Yao et al. |
| 2009/0198287 A1 | 8/2009 | Chiu |
| 2009/0209536 A1 | 8/2009 | Gahman et al. |
| 2009/0210010 A1 | 8/2009 | Strnad et al. |
| 2009/0215809 A1 | 8/2009 | Yao et al. |
| 2009/0216334 A1 | 8/2009 | Leibel |
| 2009/0222047 A1 | 9/2009 | Graham |
| 2009/0228049 A1 | 9/2009 | Park |
| 2009/0287246 A1 | 11/2009 | Cauldwell et al. |
| 2009/0291975 A1 | 11/2009 | Stern et al. |
| 2009/0292022 A1 | 11/2009 | Kowalski et al. |
| 2009/0292023 A1 | 11/2009 | Kowalski et al. |
| 2009/0306723 A1 | 12/2009 | Anapliotis et al. |
| 2010/0036430 A1 | 2/2010 | Hartdegen et al. |
| 2010/0082072 A1 | 4/2010 | Sybert et al. |
| 2010/0152752 A1 | 6/2010 | Denove et al. |
| 2010/0152786 A1* | 6/2010 | Behrbalk ................ 606/301 |
| 2010/0211071 A1 | 8/2010 | Lettmann et al. |
| 2011/0077656 A1 | 3/2011 | Sand et al. |
| 2011/0118780 A1 | 5/2011 | Holmes, Jr. |
| 2011/0178557 A1 | 7/2011 | Rush et al. |
| 2011/0224729 A1 | 9/2011 | Baker et al. |
| 2012/0016426 A1 | 1/2012 | Robinson |
| 2012/0071935 A1 | 3/2012 | Keith et al. |
| 2012/0330322 A1 | 12/2012 | Sand et al. |

FOREIGN PATENT DOCUMENTS

| | | | |
|---|---|---|---|
| EP | 284922 | A2 | 10/1988 |
| EP | 491983 | A1 | 7/1992 |
| EP | 557409 | A1 | 9/1993 |
| EP | 649447 | A1 | 4/1995 |
| EP | 757545 | A1 | 2/1997 |
| EP | 796603 | A1 | 9/1997 |
| EP | 991404 | A1 | 4/2000 |
| EP | 1044618 | A1 | 10/2000 |
| EP | 1056364 | A1 | 12/2000 |
| EP | 1113768 | A1 | 7/2001 |
| EP | 891160 | B1 | 10/2001 |
| EP | 679377 | B1 | 8/2002 |
| EP | 1287787 | A1 | 3/2003 |
| EP | 995364 | B1 | 6/2003 |
| EP | 1307116 | B1 | 5/2005 |
| EP | 1531741 | A1 | 5/2005 |
| EP | 1618806 | A1 | 1/2006 |
| EP | 1691830 | A1 | 8/2006 |
| EP | 1715888 | A2 | 11/2006 |
| EP | 1464281 | B1 | 12/2006 |
| EP | 1446028 | B1 | 1/2007 |
| EP | 1772123 | A1 | 4/2007 |
| EP | 1792577 | A1 | 6/2007 |
| EP | 1800555 | A1 | 6/2007 |
| EP | 1806062 | A1 | 7/2007 |
| EP | 1513561 | B1 | 9/2007 |
| EP | 1836981 | | 9/2007 |
| EP | 1885309 | A2 | 2/2008 |
| EP | 1913831 | A1 | 4/2008 |
| EP | 1927322 | A1 | 6/2008 |
| EP | 1587506 | B1 | 7/2008 |
| EP | 1952776 | A1 | 8/2008 |
| FR | 2893496 | A1 | 5/2007 |
| FR | 2916954 | A1 | 12/2008 |
| GB | 2023404 | A | 1/1980 |
| GB | 2228202 | A | 8/1990 |
| GB | 2269753 | A | 2/1994 |
| GB | 2337446 | A | 11/1999 |
| GB | 2425961 | A | 11/2006 |
| JP | 2071704 | A | 3/1990 |
| JP | 2295572 | A | 12/1990 |
| JP | 3188849 | A | 8/1991 |
| JP | 4108401 | A | 4/1992 |
| JP | 4129550 | A | 4/1992 |
| JP | 5329005 | A | 12/1993 |
| JP | 6054702 | A | 3/1994 |
| JP | 6054872 | A | 3/1994 |
| JP | 6062906 | A | 3/1994 |
| JP | 6105859 | A | 4/1994 |
| JP | 7031503 | A | 2/1995 |
| JP | 7039559 | A | 2/1995 |
| JP | 7241307 | A | 9/1995 |
| JP | 7255763 | A | 10/1995 |
| JP | 7308334 | A | 11/1995 |
| JP | 7323039 | A | 12/1995 |
| JP | 7324202 | A | 12/1995 |
| JP | 8131477 | A | 5/1996 |
| JP | 8150162 | A | 6/1996 |
| JP | 8154959 | A | 6/1996 |
| JP | 8243119 | A | 9/1996 |
| JP | 8299016 | A | 11/1996 |
| JP | 9010005 | A | 1/1997 |
| JP | 9010008 | A | 1/1997 |
| JP | 9028409 | A | 2/1997 |
| JP | 9051801 | A | 2/1997 |
| JP | 9075102 | A | 3/1997 |
| JP | 9140405 | A | 6/1997 |
| JP | 9191904 | A | 7/1997 |
| JP | 9215501 | A | 8/1997 |
| JP | 9276308 | A | 10/1997 |
| JP | 9313207 | A | 12/1997 |
| JP | 10043224 | A | 2/1998 |
| JP | 10052472 | A | 2/1998 |
| JP | 10155505 | A | 6/1998 |
| JP | 10155507 | A | 6/1998 |
| JP | 10155509 | A | 6/1998 |
| JP | 10155512 | A | 6/1998 |
| JP | 10168608 | A | 6/1998 |
| JP | 10234759 | A | 9/1998 |
| JP | 10328219 | A | 12/1998 |
| JP | 11012803 | A | 1/1999 |
| JP | 11032805 | A | 2/1999 |
| JP | 11056408 | A | 3/1999 |
| JP | 11076283 | A | 3/1999 |
| JP | 11146802 | A | 6/1999 |

(56) References Cited

FOREIGN PATENT DOCUMENTS

| | | |
|---|---|---|
| JP | 11169201 A | 6/1999 |
| JP | 11192103 A | 7/1999 |
| JP | 11276203 A | 10/1999 |
| JP | 11276208 A | 10/1999 |
| JP | 11279803 A | 10/1999 |
| JP | 11315401 A | 11/1999 |
| JP | 11318511 A | 11/1999 |
| JP | 2000060934 A | 2/2000 |
| JP | 2000093486 A | 4/2000 |
| JP | 2000116686 A | 4/2000 |
| JP | 2000116696 A | 4/2000 |
| JP | 2000116698 A | 4/2000 |
| JP | 2000232901 A | 8/2000 |
| JP | 2000287705 A | 10/2000 |
| JP | 2000308654 A | 11/2000 |
| JP | 2000316603 A | 11/2000 |
| JP | 2000325376 A | 11/2000 |
| JP | 2000328304 A | 11/2000 |
| JP | 2001000463 A | 1/2001 |
| JP | 2001029374 A | 2/2001 |
| JP | 2001087297 A | 4/2001 |
| JP | 2001095828 A | 4/2001 |
| JP | 2001104008 A | 4/2001 |
| JP | 2001140102 A | 5/2001 |
| JP | 2001269367 A | 10/2001 |
| JP | 2001299404 A | 10/2001 |
| JP | 2001299792 A | 10/2001 |
| JP | 2001353005 A | 12/2001 |
| JP | 2001355155 A | 12/2001 |
| JP | 2002000302 A | 1/2002 |
| JP | 2002052034 A | 2/2002 |
| JP | 2002065712 A | 3/2002 |
| JP | 2002165611 A | 6/2002 |
| JP | 2002209610 A | 7/2002 |
| JP | 2002209931 A | 7/2002 |
| JP | 2002282011 A | 10/2002 |
| JP | 2002345501 A | 12/2002 |
| JP | 2002355105 A | 12/2002 |
| JP | 2003000629 A | 1/2003 |
| JP | 2003033204 A | 2/2003 |
| JP | 2003052728 A | 2/2003 |
| JP | 2003126130 A | 5/2003 |
| JP | 2003210206 A | 7/2003 |
| JP | 2003250601 A | 9/2003 |
| JP | 2003319804 A | 11/2003 |
| JP | 2004166810 A | 6/2004 |
| JP | 2004167069 A | 6/2004 |
| JP | 2004167144 A | 6/2004 |
| JP | 2004180746 A | 7/2004 |
| JP | 2004201933 A | 7/2004 |
| JP | 2004202074 A | 7/2004 |
| JP | 2004202128 A | 7/2004 |
| JP | 2004215870 A | 8/2004 |
| JP | 2004216087 A | 8/2004 |
| JP | 2004229992 A | 8/2004 |
| JP | 2004242988 A | 9/2004 |
| JP | 2004250796 A | 9/2004 |
| JP | 2004329452 A | 11/2004 |
| JP | 2005000347 A | 1/2005 |
| JP | 2005009011 A | 1/2005 |
| JP | 2005013682 A | 1/2005 |
| JP | 2005021191 A | 1/2005 |
| JP | 2005040571 A | 2/2005 |
| JP | 2005042213 A | 2/2005 |
| JP | 2005052593 A | 3/2005 |
| JP | 2005152218 A | 6/2005 |
| JP | 2005160560 A | 6/2005 |
| JP | 2005245471 A | 9/2005 |
| JP | 2005245571 A | 9/2005 |
| JP | 2005279188 A | 10/2005 |
| JP | 2005281917 A | 10/2005 |
| JP | 2005287726 A | 10/2005 |
| JP | 2005305063 A | 11/2005 |
| JP | 2005305085 A | 11/2005 |
| JP | 2005349225 A | 12/2005 |
| JP | 2006000403 A | 1/2006 |
| JP | 2006000549 A | 1/2006 |
| JP | 2006043369 A | 2/2006 |
| JP | 2006043376 A | 2/2006 |
| JP | 2006055591 A | 3/2006 |
| JP | 2006081797 A | 3/2006 |
| JP | 2006130248 A | 5/2006 |
| JP | 2006132037 A | 5/2006 |
| JP | 2006141651 A | 6/2006 |
| JP | 2006187545 A | 7/2006 |
| JP | 2006247335 A | 9/2006 |
| JP | 2006249623 A | 9/2006 |
| JP | 2006263407 A | 10/2006 |
| JP | 2006271915 A | 10/2006 |
| JP | 2006288491 A | 10/2006 |
| JP | 2006289003 A | 10/2006 |
| JP | 2006314656 A | 11/2006 |
| JP | 2006326264 A | 12/2006 |
| JP | 2007090017 A | 4/2007 |
| JP | 2007097846 A | 4/2007 |
| JP | 2007130369 A | 5/2007 |
| JP | 2007167180 A | 7/2007 |
| JP | 2007215967 A | 8/2007 |
| JP | 2007229378 A | 9/2007 |
| JP | 2007236905 A | 9/2007 |
| JP | 2007244786 A | 9/2007 |
| JP | 2007252585 A | 10/2007 |
| JP | 2007313043 A | 12/2007 |
| JP | 2007319201 A | 12/2007 |
| JP | 2007330743 A | 12/2007 |
| JP | 2008000244 A | 1/2008 |
| JP | 2008023258 A | 2/2008 |
| JP | 2008023300 A | 2/2008 |
| JP | 2008061960 A | 3/2008 |
| JP | 2008093399 A | 4/2008 |
| JP | 2008121177 A | 5/2008 |
| WO | WO8504558 A1 | 10/1985 |
| WO | WO8901745 A1 | 3/1989 |
| WO | WO9211777 A1 | 7/1992 |
| WO | WO9401496 A1 | 1/1994 |
| WO | WO9629988 A1 | 10/1996 |
| WO | WO9641523 A1 | 12/1996 |
| WO | WO9721404 A1 | 6/1997 |
| WO | WO9858631 A1 | 12/1998 |
| WO | WO9943227 A1 | 9/1999 |
| WO | WO0006036 A1 | 2/2000 |
| WO | WO0015163 A1 | 3/2000 |
| WO | WO0018313 A1 | 4/2000 |
| WO | WO0121119 A1 | 3/2001 |
| WO | WO0191674 A1 | 12/2001 |
| WO | WO0211573 A1 | 2/2002 |
| WO | WO0217840 A1 | 3/2002 |
| WO | WO0241944 A2 | 5/2002 |
| WO | WO02098254 A1 | 12/2002 |
| WO | WO03045179 A2 | 6/2003 |
| WO | WO03099144 A1 | 12/2003 |
| WO | WO03099344 A2 | 12/2003 |
| WO | WO2004056305 A2 | 7/2004 |
| WO | WO2004058286 A1 | 7/2004 |
| WO | WO2004069866 A1 | 8/2004 |
| WO | 2004078220 | 9/2004 |
| WO | WO2004107895 A1 | 12/2004 |
| WO | WO2005013745 A1 | 2/2005 |
| WO | WO2005034670 A2 | 4/2005 |
| WO | WO2005039439 A2 | 5/2005 |
| WO | WO2005056050 A1 | 6/2005 |
| WO | WO2005079828 A2 | 9/2005 |
| WO | WO2005102092 A1 | 11/2005 |
| WO | WO2006030546 A1 | 3/2006 |
| WO | WO2006047227 A1 | 5/2006 |
| WO | WO2006058140 A2 | 6/2006 |
| WO | WO2006066419 A1 | 6/2006 |
| WO | WO2006069451 A1 | 7/2006 |
| WO | WO2006069452 A1 | 7/2006 |
| WO | WO2006088412 A1 | 8/2006 |

(56) References Cited

FOREIGN PATENT DOCUMENTS

| WO | WO2006107779 | A2 | 10/2006 |
| WO | WO2006120385 | A2 | 11/2006 |
| WO | WO2007008348 | A2 | 1/2007 |
| WO | WO2007021865 | A2 | 2/2007 |
| WO | WO2007025520 | A1 | 3/2007 |
| WO | WO2007089617 | A2 | 8/2007 |
| WO | WO2007098057 | A2 | 8/2007 |
| WO | WO2007106498 | A2 | 9/2007 |
| WO | WO2008006929 | A1 | 1/2008 |
| WO | WO2008102405 | A1 | 8/2008 |
| WO | WO2008118426 | A1 | 10/2008 |
| WO | WO2009018527 | A1 | 2/2009 |
| WO | WO2010093696 | | 8/2010 |

OTHER PUBLICATIONS

Coughlin et al., "Proximal metatarsal osteotomy and distal soft tissue reconstruction as treatment for hallux valgus deformity", Keio J. Med. 54(2) p. 60-65, 2005.

Arthrex® RetroButton™ ACL Reconstruction, 8 pages, © Copyright Arthrex Inc., 2007.

International Search Report and Written Opinion issued in PCT/US2010/023757, mailed Jun. 2, 2010, 16 pages.

International Search Report and Written Opinion issued in PCT/US2011/039041, mailed Oct. 19, 2011, 14 pages.

Invitation to Pay Additional Fees issued in PCT/US2011/039041, mailed Sep. 6, 2011, 5 pages.

* cited by examiner

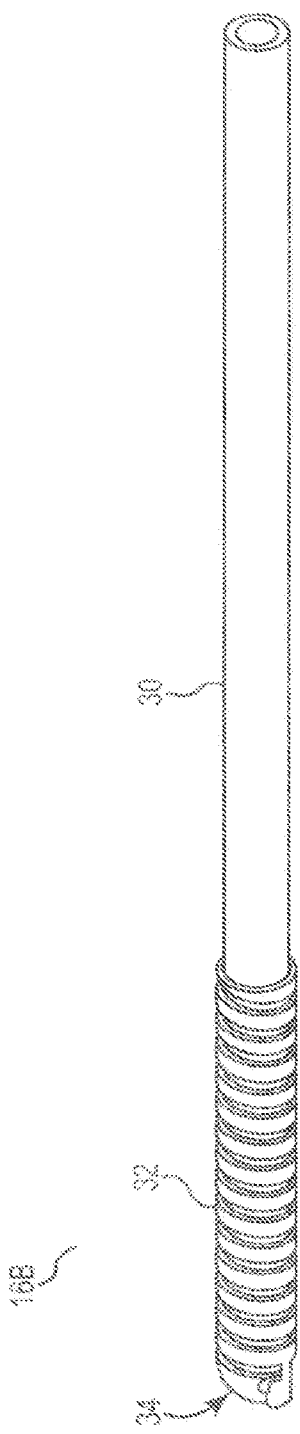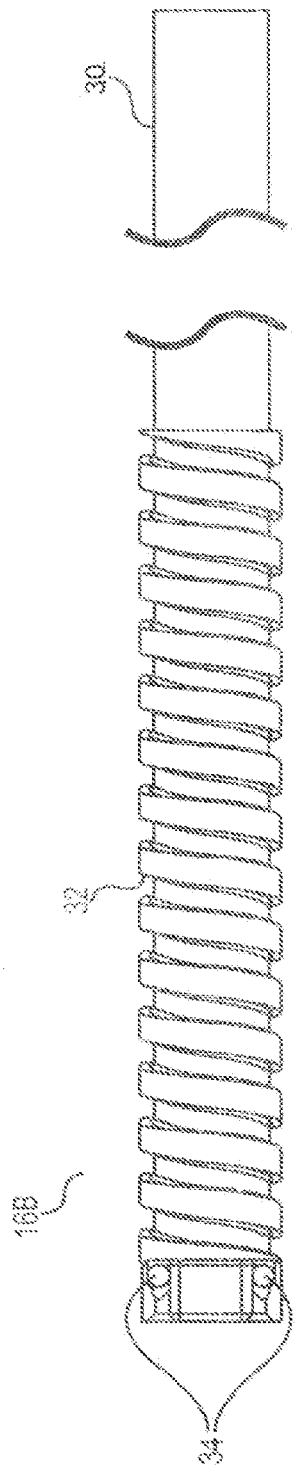
Fig. 3A
Fig. 3B

METHODS AND DEVICES FOR TREATING HALLUX VALGUS

FIELD OF THE INVENTION

The various embodiments disclosed herein relate to methods and devices for treating a structural bone and joint deformity. More specifically, certain embodiments relate to systems and methods for correcting such deformity, including hallux valgus.

BACKGROUND OF THE INVENTION

Hallux valgus deformities in the human foot typically relate to at least one of two conditions: a deviated position of the great toe where the great toe leans in towards the second toe (also referred to as the "hallux valgus angle" or "HV angle" as described below), and a deviation in the angle between the first and second metatarsal bones of the foot (also referred to as the "intermetatarsal angle" or "IM angle"). The most commonly used medical terms associated with these deformities are "hallux valgus" and "hallux abducto valgus," where "hallux" refers to the great toe, "valgus" refers to the deformity in the frontal plane of an abnormal rotation of the great toe, and "abducto" refers to the abnormal slant or leaning of the great toe towards the second toe, as shown in FIG. 1. Hallux valgus is also commonly referred to in layman's terminology as a "bunion," but the term "bunion" is more properly understood as the pathological bump, bony eminence, callous, and/or inflammation on the side of the great toe joint associated with either a bursal sac or structural deformity of the great toe as described above.

Various treatments for hallux valgus and/or bunions exist. Various surgical procedures may address some combination of removing the abnormal bony enlargement of the first metatarsal bone, realigning portions of the first metatarsal bone relative to the adjacent metatarsal bone via an osteotomy, straightening the first metatarsal bone relative to the adjacent toes through manipulations of the joint capsule, realigning the cartilaginous surfaces of the great toe joint, and/or repositioning the sesamoid bones beneath the first metatarsal bone. Other treatments can include bunion pads and external splints. All of these known treatments have shortcomings in either effectiveness (pads and splints) or invasiveness (the surgical procedures). With respect to the existing surgical procedures, the vast majority require an osteotomy for realignment of portions of the first metatarsal bone, which leads to long recovery and the need for patients to wear a cast or surgical boot for weeks following the operation, as well as the need to "stage" the procedure if both feet require surgical correction, i.e., treating one foot in a first surgery and then the other in a subsequent second surgery. Further, the surgical patients are left with a significant scar and poor cosmesis. In addition, studies have highlighted that as many as 30% of bunion surgery patients are unhappy with the result and nearly 10% have post-surgical complications. Finally, the surgical procedures are costly, requiring anesthesia, a lengthy operating time, and multiple trained medical staff.

Thus, there is a need in the art for improved methods and devices for treating hallux valgus.

BRIEF SUMMARY OF THE INVENTION

Discussed herein are various treatment devices for treating structural bone deformities.

In Example 1, a method of treating hallux valgus comprises positioning a first bone anchor in a second metatarsal bone, wherein the first bone anchor is coupled to a first end of a tether, deploying prongs within the second metatarsal bone, positioning a second bone anchor in a medial side of a first metatarsal bone and coupling the second bone anchor to a second end of the tether, and urging the second bone anchor distally in relation to the tether. The step of deploying the prongs is such that the prongs are positioned at a predetermined depth within the second metatarsal bone such that the prongs are substantially not in contact with cortical bone. The prongs are operably coupled to the first bone anchor. The urging of the second anchor distally thereby urges the second bone anchor toward the first bone anchor.

Example 2 relates to the method of treating hallux valgus according to Example 1, wherein urging the second bone anchor distally in relation to the tether further comprises rotating the second bone anchor.

Example 3 relates to the method of treating hallux valgus according to Example 1, wherein positioning a first bone anchor further comprises positioning a deployment assembly through a hole formed in the first metatarsal bone and into contact with the second metatarsal bone. The deployment assembly has an outer tube and a deployment tube disposed within the outer tube. The tether is disposed within the outer tube and has a flexible component and a base component coupled to the flexible component. The first bone anchor is disposed at the distal end of the outer tube and is coupled to the first end of the flexible component. The deployment tube has a deployment anvil disposed at the distal end of the deployment tube.

Example 4 relates to the method of treating hallux valgus according to Example 3, wherein the deploying the prongs comprises urging the deployment tube in a proximal direction, whereby the deployment anvil is urged against the first bone anchor.

Example 5 relates to the method of treating hallux valgus according to Example 3, wherein the coupling the second bone anchor to the second end of the tether further comprises coupling the second bone anchor to a proximal end of the base component.

Example 6 relates to the method of treating hallux valgus according to Example 5, wherein the coupling the second bone anchor to the proximal end of the base component further comprises using an anchor placement tool to couple the second bone anchor to the proximal end of the base component.

Example 7 relates to the method of treating hallux valgus according to Example 1, and further comprises forming a hole in the first metatarsal bone prior to positioning the first bone anchor in the second metatarsal bone.

Example 8 relates to the method of treating hallux valgus according to Example 1, and further comprises first positioning a guide wire through the first metatarsal bone and into the second metatarsal bone, wherein the positioning the first bone anchor comprises positioning the first bone anchor over the guide wire.

In Example 9, a method of treating hallux valgus comprises positioning a first bone anchor in a second metatarsal bone, wherein the first bone anchor comprises at least one undeployed prong, deploying the at least one prong at a depth within the second metatarsal bone such that the at least one prong is positioned solely within cancellous bone of the second metatarsal bone, and positioning a second bone anchor in a first metatarsal bone and coupling the second bone anchor to a second end of the tether. The first bone anchor is coupled to a first end of the tether. The at least one prong extends from the first bone anchor such that at least a portion of the at least one prong is closer to parallel to a longitudinal axis of the second metatarsal than perpendicular.

Example 10 relates to the method of treating hallux valgus according to Example 9, and further comprises forming a hole in the first metatarsal bone prior to positioning the first bone anchor in the second metatarsal bone.

Example 11 relates to the method of treating hallux valgus according to Example 10, wherein positioning the first bone anchor in the second metatarsal bone further comprises first inserting the first bone anchor through the hole in the first metatarsal bone.

Example 12 relates to the method of treating hallux valgus according to Example 9, wherein the positioning the first bone anchor further comprises positioning a deployment assembly through a hole formed in the first metatarsal bone. The deployment assembly has an outer tube and a deployment tube disposed within the outer tube. The tether is disposed within the outer tube and has a flexible component and a base component coupled to the flexible component. The first bone anchor is disposed at the distal end of the outer tube and is coupled to the first end of the flexible component. The deployment tube has a deployment anvil that is disposed at the distal end of the deployment tube and is distal to the first bone anchor.

Example 13 relates to the method of treating hallux valgus according to Example 12, wherein the deploying the at least one prong comprises urging the deployment tube in a proximal direction, whereby the deployment anvil is urged against the first bone anchor.

Example 14 relates to the method of treating hallux valgus according to Example 13, wherein the urging the deployment anvil against the first bone anchor urges the at least one prong from an undeployed position to a deployed position.

Example 15 relates to the method of treating hallux valgus according to Example 9, and further comprises first positioning a guide wire through the first metatarsal bone and into the second metatarsal bone, wherein the positioning the first bone anchor comprises positioning the first bone anchor over the guide wire.

In Example 16, a method of treating hallux valgus comprises forming a hole in a first metatarsal bone, inserting a deployment assembly into the hole in the first metatarsal bone, positioning a first bone anchor in a second metatarsal bone, deploying at least one prong within the second metatarsal bone, removing the deployment assembly, and positioning a second bone anchor in a first metatarsal bone and coupling the second bone anchor to a second end of the tether. The deployment assembly has an outer tube, the tether disposed within the outer tube, a first bone anchor disposed at the distal end of the outer tube, and a deployment tube disposed within the outer tube. The tether has a flexible component and a base component coupled to the flexible component. The first bone anchor is coupled to the first end of the flexible component and has at least one undeployed prong. The deployment tube has a deployment anvil that is disposed at the distal end of the deployment tube and is distal to the first bone anchor.

Example 17 relates to the method of treating hallux valgus according to Example 16, wherein the positioning the first bone anchor further comprises rotating the deployment assembly to drill the first bone anchor into the second metatarsal bone.

Example 18 relates to the method of treating hallux valgus according to Example 16, wherein deploying the at least one prong further comprises deploying the at least one prong such that the at least one prong extends from the first bone anchor such that at least a portion of the at least one prong is closer to parallel to a longitudinal axis of the second metatarsal than perpendicular to the longitudinal axis.

Example 19 relates to the method of treating hallux valgus according to Example 16, and further comprises urging the second bone anchor distally in relation to the tether, thereby urging the second bone anchor toward the first bone anchor.

Example 20 relates to the method of treating hallux valgus according to Example 16, wherein the deploying the at least one prong comprises urging the deployment tube in a proximal direction in relation to the outer tube, whereby the deployment anvil is urged against the first bone anchor.

Example 21 relates to the method of treating hallux valgus according to Example 20, wherein the urging the deployment anvil against the first bone anchor urges the at least one prong from an undeployed position to a deployed position.

Example 22 relates to the method of treating hallux valgus according to Example 16, and further comprises first positioning a guide wire through the first metatarsal bone and into the second metatarsal bone, wherein the forming the hole in the first metatarsal bone further comprises positioning a drill over the guide wire and drilling the hole in the first metatarsal bone, and wherein the inserting the deployment assembly into the hole further comprises inserting the deployment assembly over the guide wire.

In Example 23, a bone anchor comprises a substantially cylindrical body, a lumen disposed throughout a length of the cylindrical body, a distal opening defined in a distal end of the cylindrical body and in communication with the lumen, a proximal opening defined in a proximal end of the cylindrical body and in communication with the lumen, and a deployment section proximal to the distal end of the cylindrical body. The deployment section has a pre-deployment cylindrical configuration and a deployment configuration, The deployment configuration has at least two prongs extending away from the cylindrical body that are configured to be positioned in cancellous bone.

Example 24 relates to the bone anchor according to Example 23, wherein at least a portion of each of the at least two prongs is perpendicular to a longitudinal axis of the cylindrical body.

Example 25 relates to the bone anchor according to Example 23, wherein the distal opening further comprises a beveled configuration configured to receive a deployment anvil.

Example 26 relates to the bone anchor according to Example 23, wherein the distal opening further comprises at least two notches defined along an edge of the opening, wherein the at least two notches define weak points at the distal opening.

Example 27 relates to the bone anchor according to Example 23, wherein the pre-deployment cylindrical configuration is configured to be deformed into the deployment configuration.

Example 28 relates to the bone anchor according to Example 27, wherein the pre-deployment cylindrical configuration is configured to be deformed into the deployment configuration by a deployment anvil.

Example 29 relates to the bone anchor according to Example 23, wherein a deployment anvil disposed at the distal opening is configured to move from a distal position to a proximal position, whereby the pre-deployment configuration is configured to be deformed into the deployment configuration.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3A is a perspective view of a tether base component, according to one embodiment.

FIG. 3B is a side view of the tether base component of FIG. 3A, according to one embodiment.

DETAILED DESCRIPTION

Various embodiments disclosed herein relate to methods and devices for treating a bone deformity, such as, for example, hallux valgus (bunions). More specifically, various embodiments herein relate to bone deformity treatments using tension or connection systems and methods for anchoring or otherwise coupling metatarsal bones such as the first and second metatarsal bones. Some of the various device and method embodiments disclosed herein operate at least in part by anchoring or coupling to the heads of the first and second metatarsal bones. As such, various embodiments disclosed herein provide systems and methods for implantation of treatment devices and treatment of hallux valgus with reduced trauma and quicker recovery in comparison to known systems and treatments.

Figure 1:
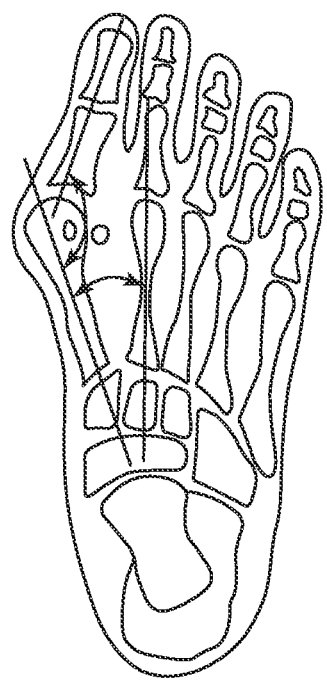
FIG. 1 is a schematic depiction of a foot exhibiting hallux valgus.
Figure 2:
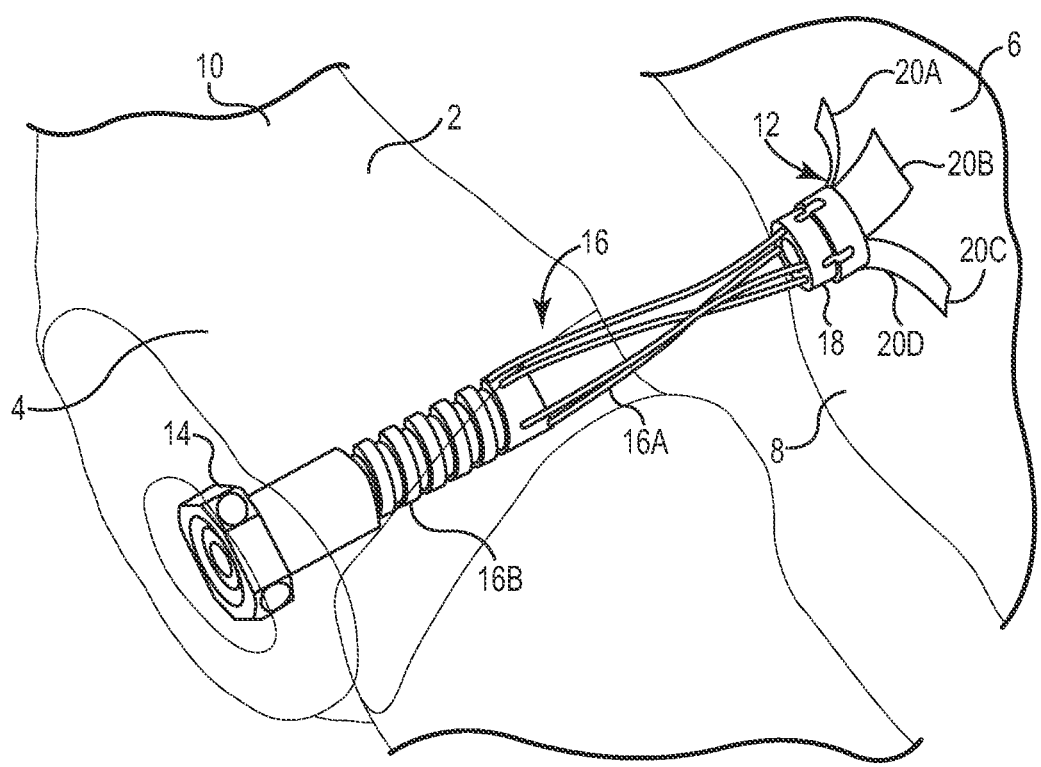
FIG. 2 is a schematic depiction of an implantable bone deformity treatment device in a patient's foot, according to one embodiment.

FIG. 2 depicts one embodiment of a device or system 10 coupling the first and second metatarsals of a foot. In this figure, the device 10 is an implant having a first anchor 12 positioned in the second metatarsal 6 and a second anchor 14 positioned in the first metatarsal 2. In one implementation, the first anchor 12 is positioned in the head 8 of the second metatarsal 6 and the second anchor 14 is positioned in the head 4 of the first metatarsal 2. Alternatively, the anchors 12, 14 can be positioned anywhere along the metatarsals. In this embodiment, the first anchor 12 is a pronged bone anchor 12 and the second anchor 14 is an internally-threaded bone anchor 14. Alternatively, the anchors 12, 14 can take a variety of known forms, including several discussed below. In addition, the device 10 has a tether 16 coupling the first and second anchors 12, 14, as will be described in further detail herein. It is understood that each of the various device and method embodiments disclosed herein can be the sole treatment for the bone deformity. It is further understood that any of these embodiments could also be used in conjunction with any one or more of other known treatments, such as surgical repositioning of the bones, surgical removal of the underlying bunion, pads, splints, or any other treatment method or device.

It is understood that the term "bone anchor" (or, alternatively, "anchor"), as used herein, is intended for purposes of this application to mean any component or device that can be used with any of the treatment device embodiments disclosed herein for anchoring or coupling such treatment devices to a bone. It is also understood that "tether," as used herein, is intended to mean any elongate component for use with medical devices such as suture, thread, a tube, or any other such material or device or combination thereof that can couple or be tensioned between two components such as anchors to treat bone deformations. In addition, it is understood that "prong," as used herein, is intended for purposes of this application to mean any component or device that projects or extends from a bone anchor and is intended to enhance fixation of the anchor in the bone.

The pronged anchor 12 embodiment as shown in FIG. 2 has an anchor base 18 with four prongs 20A, 20B, 20C, 20D extending from the base 18. Alternatively, the anchor 12 can have one prong, two prongs, three prongs, or more than four prongs. In this embodiment, the prongs 20 are deployable prongs that are deployed using a method and apparatus described in further detail below. Alternatively, the prongs can be deployable by any known method using any known apparatus. In the embodiment shown in FIG. 2, the prongs 20 or portions thereof extend from the base 18 in a direction that is substantially perpendicular to, or at least not parallel with, the longitudinal axis of the device 10. Alternatively, the prongs 20 extend from the base 18 such that at least a portion of each prong 20 is substantially perpendicular to the longitudinal axis of the device 10. In a further alternative, the prongs 20 extend from the base 18 such that at least a portion of each prong 20 is closer to a position that is perpendicular to the longitudinal axis of the device 10 than a position that is parallel to that axis. In yet another alternative, a substantial portion of the length of each of the prongs 20 is not parallel to the longitudinal axis of the device 10. According to another embodiment, each of the prongs 20 extend out from the base 18 such that each prong protrudes away from the base 18 such that the distance from the distal end of one prong 20 to the distal end of another 20 is greater than the diameter of the base 18. In another implementation, each of the prongs 20 extends out from the base 18 such that at least a portion of each prong is substantially parallel to a longitudinal axis of the second metatarsal 6 or at least closer to parallel to the longitudinal axis than perpendicular.

In accordance with one implementation, the positioning of the prongs 20 can help to secure the anchor 12 in the head 8 of the second metatarsal 6. That is, the head 8 of the second metatarsal 6 is comprised of a substantial amount of cancellous bone surrounded by a relatively thin layer of cortical bone. In comparison, other portions of the second metatarsal bone 6 along the length of the bone have a greater amount of cortical bone, which is denser and less fragile (more resistant to breaking or having a greater ability to withstand point loads) than cancellous bone. As such, in comparison to the shaft of the second metatarsal 6, the head 8 has a greater percentage of cancellous bone and thus a greater percentage of porous bone. Given the greater porosity of the head 8 portion of the second metatarsal bone 6, fixation of any prong or other fixation mechanism can be more difficult in comparison to denser bone. As such, it is beneficial that any anchor being positioned in the head have deployable prongs such as those shown in FIG. 2 that extend away from the anchor base such that the diameter of the deployed prongs 20 is greater than the base 18 or the undeployed prongs 20 and/or such that the deployed prongs 20 are positioned in the head 8 such that at least a portion of each prong 20 is perpendicular to the longitudinal axis of the device 10, thereby providing greater stability or fixation for the anchor 12 in the head 8 of the second metatarsal bone 6.

It is also beneficial, according to one embodiment, that the deployed prongs 20 be positioned at some depth in the head 8. More specifically, it is beneficial that the prongs 20 are not positioned at or near the medial surface of the head 8 such that the prongs 20 are in contact with the medial cortical bone surrounding the cancellous bone in the head 8, which places undue stress on the cortical bone if some external force is applied to the patient's metatarsals. As such, in one implementation, the deployed prongs 20 are positioned at a depth that ranges from at least about 2 mm to at least about 10 mm from the surface of the head 8. Alternatively, the prongs 20 are positioned from at least about 4 mm to at least about 8 mm from the surface.

In accordance with one implementation, one possible advantage of positioning the anchors 12, 14 in the metatarsal heads 4, 8 is the reduced stress loading in the metatarsal heads 4, 8. That is, it is understood that the metatarsal shafts are subjected to extreme outside forces that result in a great deal of stress on the shafts in comparison to the heads. It may therefore be advantageous to avoid any mechanical compromise to the shafts of the metatarsals 2, 6, which could lead to stress fractures of the shafts. As such, the metatarsal bones 2, 6 are subject to less risk of stress fracture when the anchors 12, 14 are positioned in the metatarsal heads 4, 8.

According to another embodiment, another possible advantage of positioning the anchors 12, 14 in the metatarsal heads 4, 8 as opposed to the shafts is that larger anchors can be used, because the heads 4, 8 are larger and thus have greater volume in comparison to the metatarsal shafts. That is, given the greater amount of space available in the heads 4, 8, larger anchors can be implanted in the heads 4, 8. Given that larger anchors can have greater fixation strength in comparison to smaller anchors, implantation in the heads 4, 8 can mean greater anchoring strength.

In the embodiment of FIG. 2, the tether 16 coupled to the first and second anchors 12, 14 has two components: a flexible component 16A and a base component 16B. The flexible component 16A is coupled at the distal end to the first anchor base 18 and at the proximal end to the tether base component 16B. More specifically, at the distal end, the sutures 16A are positioned in holes (not shown) in the anchor base 18 and thereby coupled to the anchor base 18. At the proximal end, the sutures 16A are positioned in holes (not shown) in the distal end of the tether base component 16B. Alternatively, the flexible component 16A can be coupled to the bases 18, 16B in any known fashion using any known coupling components or methods. In the specific embodiment shown in FIG. 2, the flexible component 16A is a set of four suture lines, each of which is individually coupled to the first anchor base 18 and the tether base 16B as shown. Alternatively, the flexible component 16A can be a single suture line that is looped through the holes in both the first anchor base 18 and the tether base 16B. In a further alternative, the flexible component 16A can be one suture, two sutures, three sutures, four sutures, or more than four sutures.

In one alternative implementation, the flexible component 16A can have a predetermined failure point such that it will fail at some predetermined amount of applied force that is lower than the anticipated anchoring force of the first anchor 12 in the head 8 of the second metatarsal bone 6 or the second anchor 14 in the head 4 of the first metatarsal bone 2. For example, if the expected anchoring forces of the first anchor 12 and second anchor 14 are 60 pounds, the flexible component 16A can be designed to break at a lower force, such as, for example, 50 pounds. As such, if the device is exposed to an unusually high biomechanical force, such as an unexpected fall by the patient, the flexible component 16A in this embodiment is designed to fail before the high force causes the first anchor 12 or second anchor 14 to be pulled from their respective implantation sites. Although the result is a failure of the tether 16, it is understood that it is easier to repair the failed tether 16 rather than repair the substantial damage resulting from an anchor being pulled out of the bone.

In yet another alternative, the flexible component 16A can be any number of individual pieces of a variety of suitable implantable materials. Such materials include monofilament or multi-filament structures such as yarns, braids, or weaves. In accordance with one embodiment, the tether has lateral flexibility, and as such, materials that could provide lateral flexibility include polyester (such as Dacron™), ultra-high molecular weight polyethylene (UHMWPE), high strength expanded PTFE, or polycarbonate urethane. Other materials include those exhibiting higher elasticity, such as silicone rubber, PEBA such as Pebax™, Kraton™ polymers, polyurethane, latex, or any other elastomeric materials. In other implementations, the tether embodiments can be made of a bio-absorbable material such as poly-lactic acid, poly-L-lactic acid, or any known bioabsorbable material such as those used in biodegradable sutures. It is understood that various combinations of the above materials are also contemplated.

FIGS. 3A and 3B further depict the tether base component 16B. The component 16B has a non-threaded portion 30, a threaded portion 32, and holes 34 defined at or near the distal end. The holes 34 are configured to receive the sutures 16A of the flexible component 16A as described above. Alternatively, the distal end of the base component 16B has any known coupling mechanism to couple to any known flexible component 16A. The threaded portion 32 is configured to engage with the threaded lumen of the second anchor 14 as described in further detail below, and the non-threaded portion 30 extends proximally from the threaded portion 32. In an alternative embodiment, the portion 32 can have any other known mechanism for engaging with the second anchor 14 instead of threads. In one embodiment, the tether base component 16B is comprised of polyether ether ketone ("PEEK"). Alternatively, the component 16B can be made of any suitable biocompatible material, such as stainless steel, titanium, cobalt alloy, polyester, PTFE, nylon, HDPE, or the like.

Alternatively, instead of two components 16A, 16B, the tether 16 can be a single component. In a further alternative, the tether 16 can be any known elongate device or structure for coupling two bone anchors. In one implementation, the tether can be any tether or tether material as described in U.S. application Ser. No. 12/371,354, filed on Feb. 13, 2009 and entitled "Methods and Devices for Treating Hallux Valgus;" U.S. application Ser. No. 12/567,314, filed on Sep. 25, 2009 and entitled "Methods and Devices for Treating A Structural Bone and Joint Deformity;" or U.S. application Ser. No. 12/691,646, filed on Jan. 21, 2010 and entitled "Methods and Devices for Treating Hallux Valgus," each of which is hereby incorporated herein by reference in its entirety.

Figure 4A:
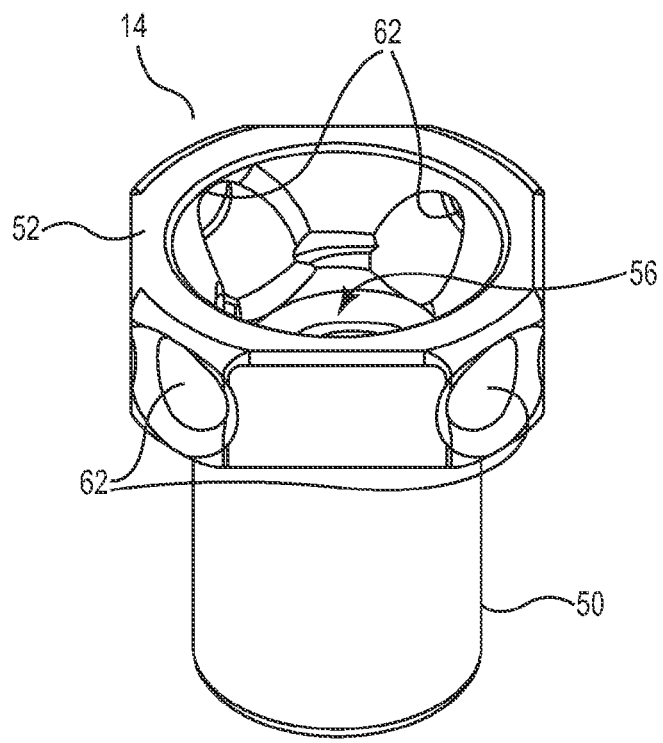
FIG. 4A is a perspective view of a bone anchor, according to one embodiment.
Figure 4B:
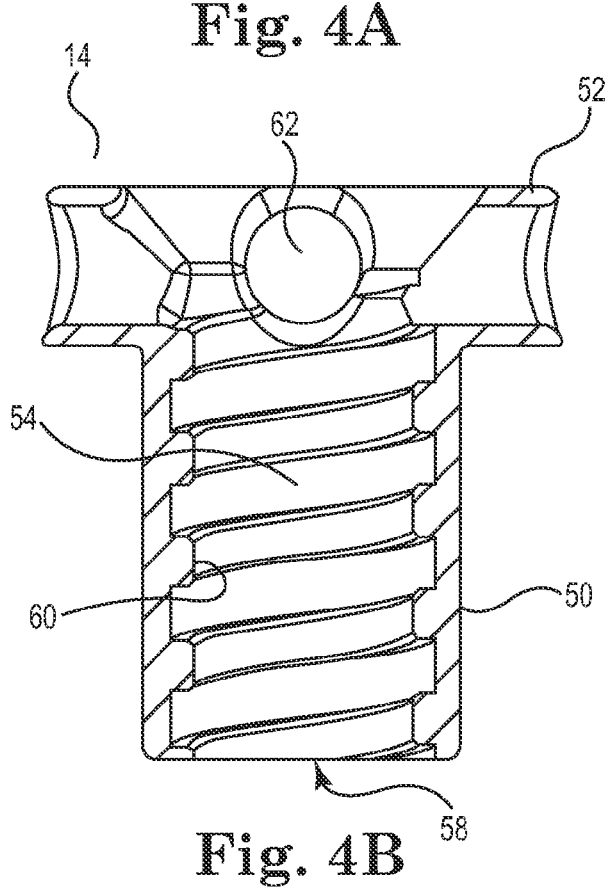
FIG. 4B is a cross-sectional side view of the bone anchor of FIG. 4A, according to one embodiment.

As mentioned above, the second anchor 14 is coupled to the tether base component 16B. FIGS. 4A and 4B further depict the second anchor 14. In this embodiment, the anchor 14 has a body 50 and a head 52 with a lumen 54 defined within both the body 50 and head 52. An opening 56 to the lumen 54 is defined in the head 52 and an opening 58 to the lumen 54 is defined in the body 50. In the embodiment shown, the body 50 has threads 60 in the lumen 54. The threads 60 are configured to engage with the threads 32 of the tether base component 16B. In a further alternative, the anchor body 50 is attached to the bone 2 by any known attachment method, material, or device, such as, for example, a porous outside surface that facilitates bony in-growth. Additionally, the body 50 can also have any known mechanism for engaging with the tether base component 16B.

Continuing with the embodiment of FIGS. 4A and 4B, there are four holes 62 defined in the head 52. According to one implementation, the holes 62 are configured to receive sutures for purposes of coupling the sutures to the tissue of the medial portion of the metatarsophalangeal ("MTP") capsule on the first metatarsal and tightening the sutures, thereby "tightening" or foreshortening the capsule as described in further detail below. It is understood that, while depicted in a particular configuration in FIGS. 4A and 4B, the four holes 62 can be defined in the head in any known shape, configuration, or position on the head 52. Alternatively, there can be one hole, two holes, three holes, or more than four holes defined in the head 52. In a further alternative, the head 52 can have no holes or can have any known mechanism for purposes of tightening the MTP capsule.

Alternatively, the second anchor 14 can be the same as or similar to the threaded bone anchor embodiments disclosed in U.S. application Ser. Nos. 12/691,646 or 12/567,314, both of which are incorporated by reference above.

It is understood that any of the first anchor embodiments contemplated herein can be made of any suitable material, including plastically deformable materials, biocompatible polymers, relatively rigid polymeric materials, or metals. Specific examples can include stainless steel, MP35N, titanium and titanium alloys, nitinol, plastic, UHMWPE, cross-linked UHMWPE, PEEK, polycarbonate, polylactic acid (PLLA or PDLA), bone allograft, hydoxyapatite coral coated for ingrowth, human dermis, porcine intestinal mucosa, fetal bovine skin, porcine skin, cadaveric fascia, marlex mesh, hernia mesh, polytetrafluorethylene, absorbable suture, or umbilical tape. According to one embodiment, a first anchor having prongs is formed of commercially pure titanium.

It is further understood that any of the second bone anchor embodiments contemplated herein can be made of any known material that is suitable for implantable medical components or devices. In one embodiment, the second bone anchor can be made of a relatively rigid material such as stainless steel, titanium, a rigid polymer such as PEEK, or the like.

Figure 5:
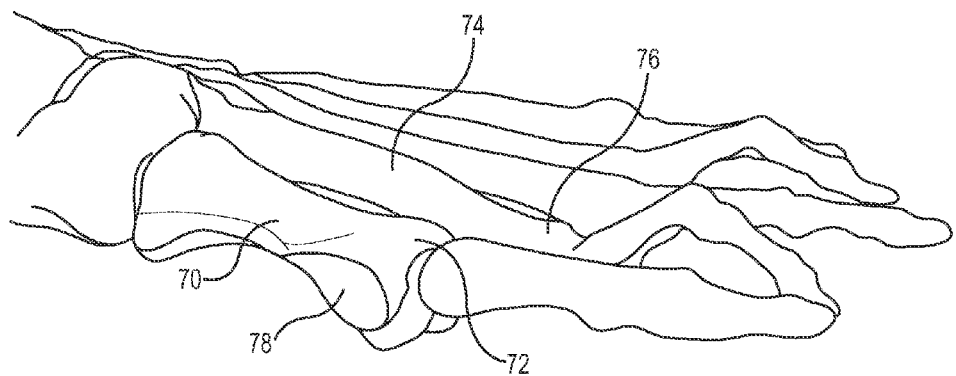
FIG. 5 is a schematic depiction of a foot in which the eminence has been removed, according to one embodiment.
Figure 6:
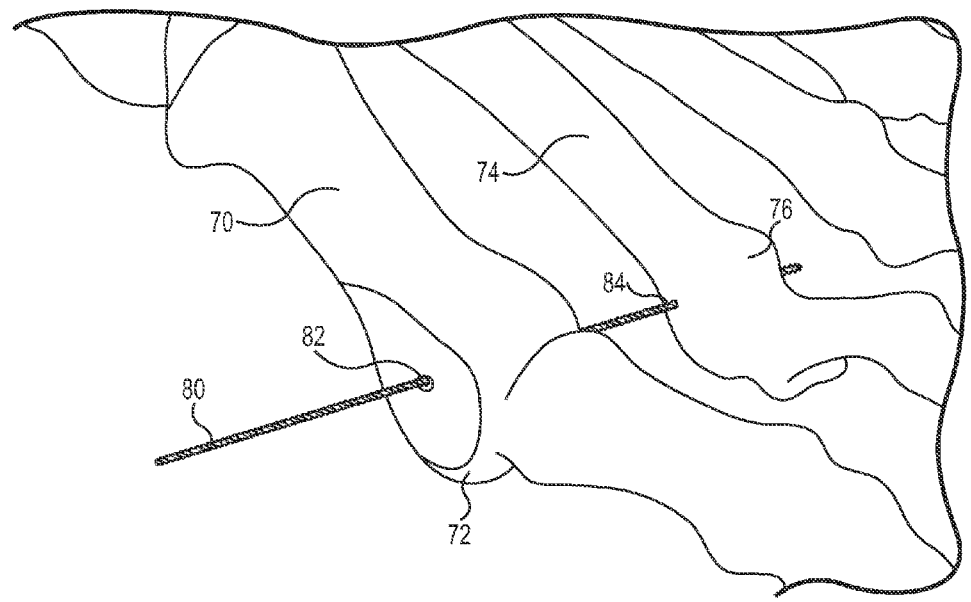
FIG. 6 is a schematic depiction of the foot of FIG. 5, in which a guide wire has been inserted through the first and second metatarsal bones, according to one embodiment.

Various implantation methods, systems, and devices can be used to implant treatment devices similar to that depicted in FIG. 2. In accordance with one embodiment, a treatment device can be implanted in the following manner. First, as shown in FIG. 5, a portion or all of the eminence on the first metatarsal 70 is removed by conventional methods, thereby resulting in a flat surface 78 where the eminence had been. Note that in FIG. 5 and subsequent figures, soft tissue such as skin and the joint capsular tissue is not shown, but it is understood to be present. In an alternative embodiment, the eminence is not removed. Next, a guide wire 80 is positioned into and through the first and second metatarsals 70, 74 as shown in FIG. 6. In the figure, the guide wire 80 is shown extending through the second metatarsal 74 and projecting from the lateral side of the metatarsal 74. Alternatively, the guide wire 80 does not extend all the way through the second metatarsal 74. In one embodiment, the guide wire 80 is a known guide wire for bone surgery that can be inserted through the bone, forming holes 82, 84. The guide wire 80 is inserted using a hand drill or a power drill according to known procedures. The guide wire 80 is positioned through the heads 72, 76 of the first and second metatarsals 70, 74. Alternatively, the guide wire 80 can be positioned anywhere in the first and second metatarsals.

According to one implementation, the guide wire 80 has a size ranging from about 0.010 inch to about 0.050 inch. Alternatively, the guide wire 80 ranges from about 0.030 inch to about 0.040 inch in size. In a further alternative, the guide wire 80 is a known "K-wire" (also referred to as a "Kirschner wire") that is typically used in bone surgeries.

In some implementations, the proper positioning of the guide wire 80 is then confirmed using a known fluoroscopic verification procedure. Alternatively, any known procedure can be used to confirm the positioning of the wire 80. In a further alternative, the positioning is not confirmed.

Figure 7:
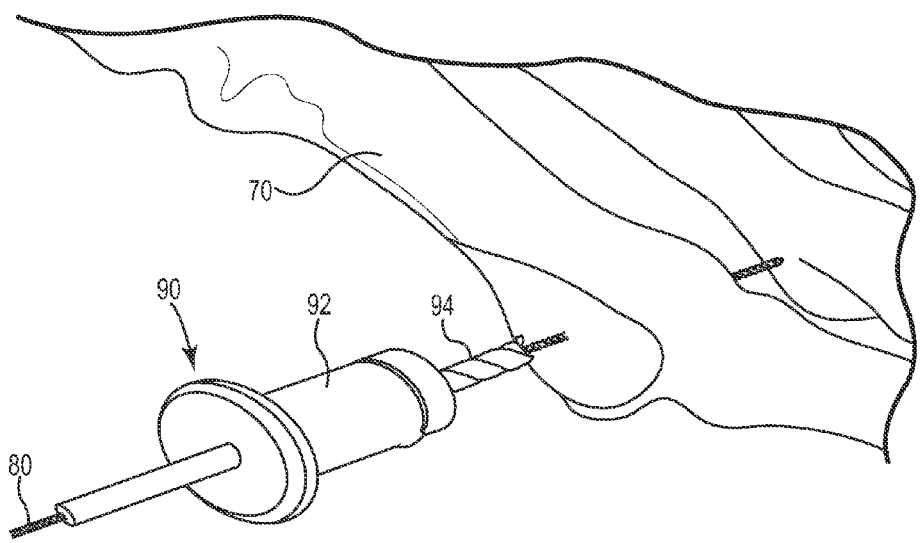
FIG. 7 is a schematic depiction of the foot of FIG. 6, in which a drill has been positioned over the guide wire, according to one embodiment.
Figure 8:
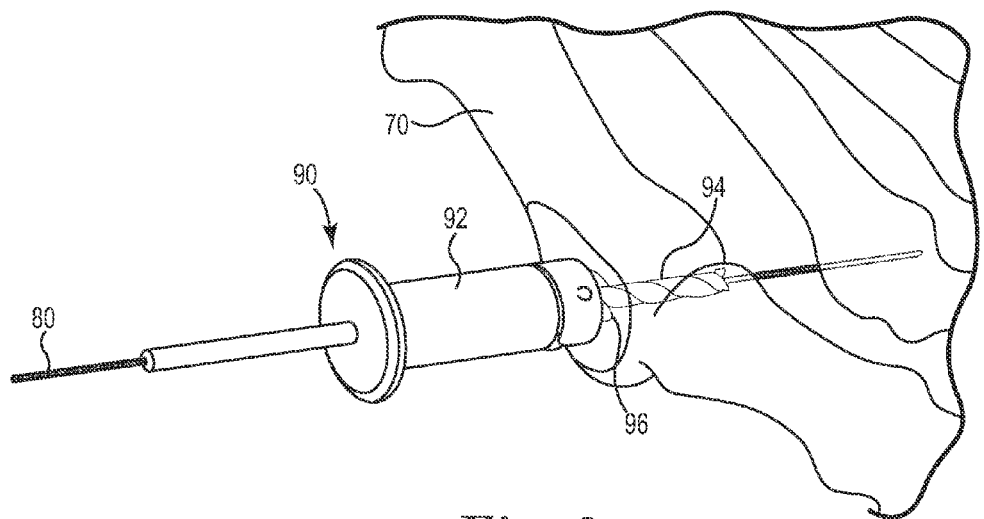
FIG. 8 is a schematic depiction of the foot of FIG. 7, in which the drill has been drilled into the first metatarsal bone, according to one embodiment.
Figure 9A:
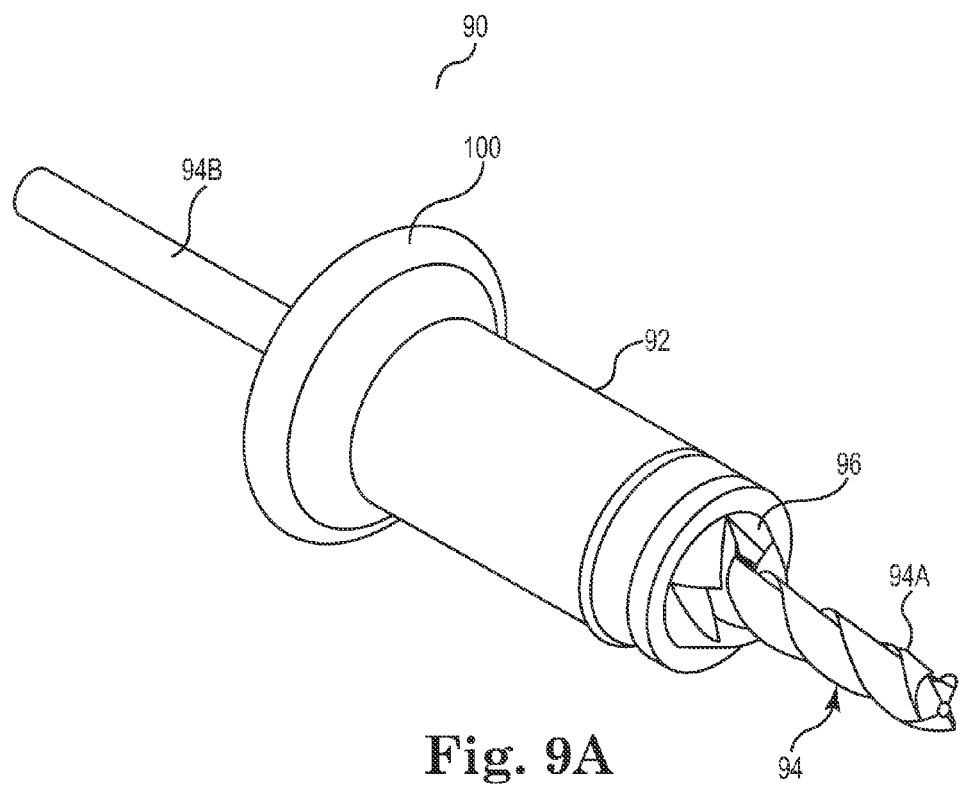
FIG. 9A is a perspective view of a drill, according to one embodiment.
Figure 9B:
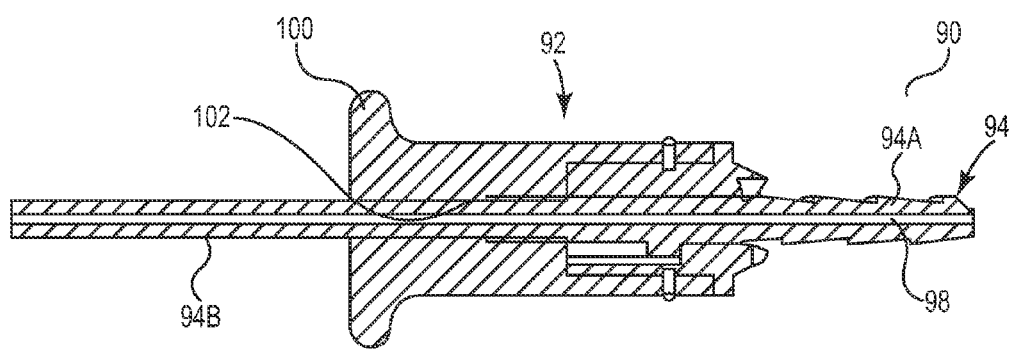
FIG. 9B is a cross-sectional side view of the drill of FIG. 9A, according to one embodiment.

In one embodiment as shown in FIGS. 7 and 8, the next step is to drill a hole with a counterbore in the first metatarsal 70. According to one embodiment, the drill 90 depicted in FIGS. 9A and 9B can be used. The drilling device 90 has a body 92, a cannulated drill bit 94, and a counterbore drill bit 96. The cannulated drill bit 94 has a fluted portion 94A and a shank 94B extending proximally from the fluted portion 94A. The cannulated drill bit 94 extends through a central lumen 102 of the body 92 and defines a lumen 98 defined along its entire length. The drilling device 90, in one embodiment, has an adjustment knob 100 that is rotatable in relation to the cannulated drill bit 94 such that the portion of the cannulated drill bit 94 extending distally from the body 92 can be adjusted. More specifically, the rotation of the adjustment knob 100 in relation to the drill bit 94 results in the rotation of threads (not shown) on the central lumen 102 that engage with threads (not shown) on the cannulated drill bit 94, thereby moving the drill bit 94 axially in relation to the body 92. Alternatively, any known bone drilling mechanism that can drill a hole with a counterbore can be used in this procedure. In a further alternative, a hole can be formed without a counterbore.

In use, the drilling mechanism 90 is used to drill the cannulated drill bit 94 and the counterbore drill bit 96 into the first metatarsal 70 as shown in FIGS. 7 and 8. As shown in FIG. 7, the drilling mechanism 90 is positioned over the guide wire 80 for purposes of the drilling step. More specifically, the guide wire 80 is inserted into the lumen 98 in the cannulated drill bit 94 such that the drilling mechanism 90 can be moved over the guide wire 80. In this manner, the guide wire 80 can be used to position the drilling mechanism 90 correctly.

Figure 10:
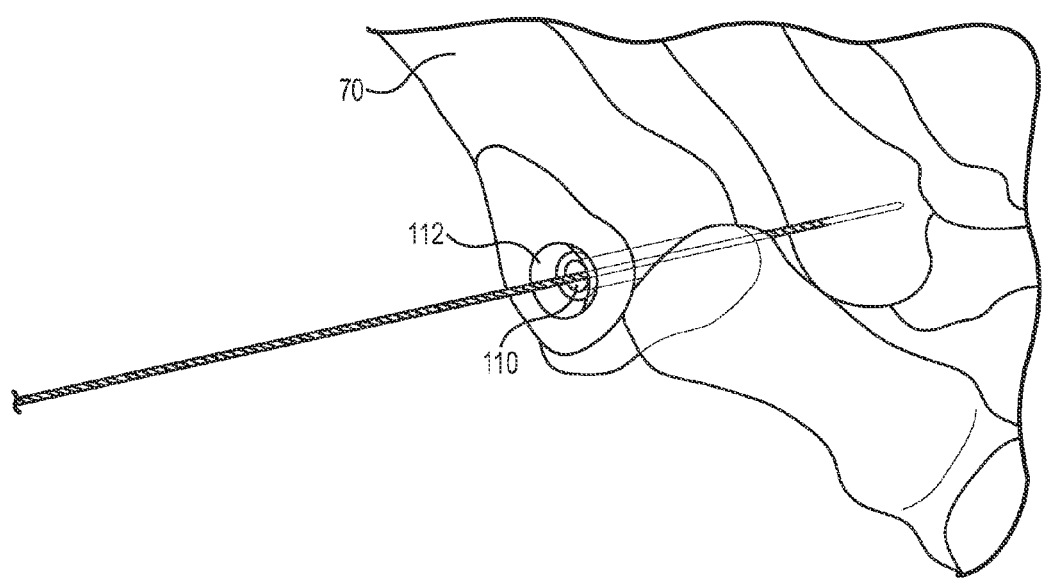
FIG. 10 is a schematic depiction of the foot of FIG. 8, in which the drilling is complete and the drill has been removed, according to one embodiment.

The resulting lumen 110 through the first metatarsal 70 with the counterbore 112 is shown in FIG. 10. In an alternative implementation, any known method or apparatus that can form the lumen 110 with the counterbore 112 can be used. In a further embodiment, the lumen 110 can be formed without a counterbore.

Figure 11A:
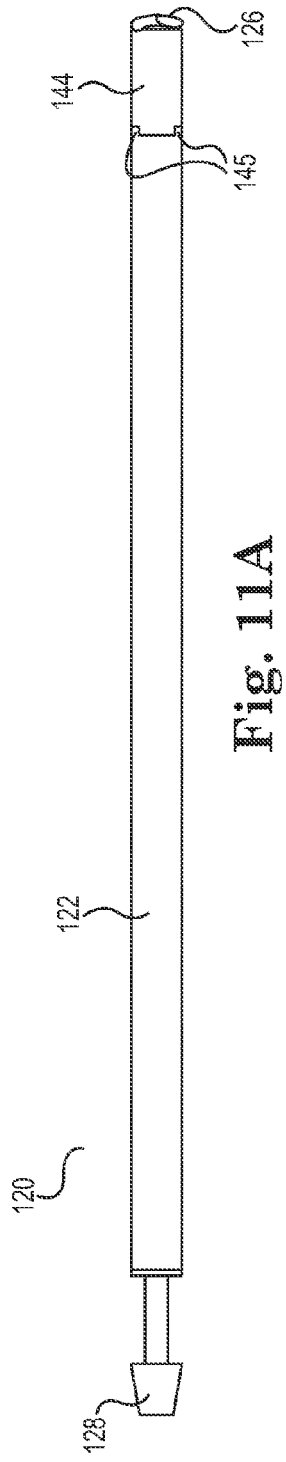
FIG. 11A is a side view of a deployment assembly, according to one embodiment.
Figure 11B:
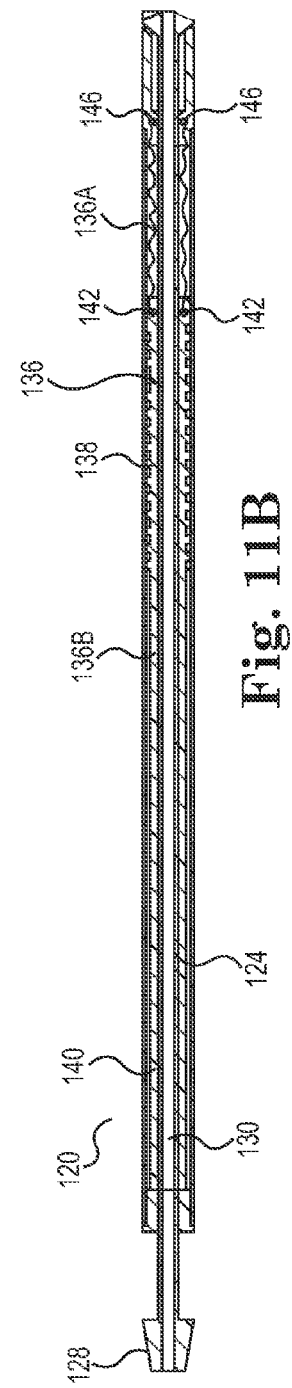
FIG. 11B is a cross-sectional side view of the deployment assembly of FIG. 11A, according to one embodiment.
Figure 11C:
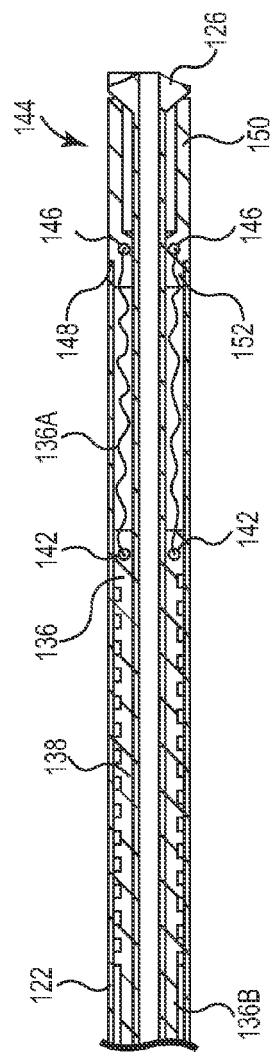
FIG. 11C is a expanded cross-sectional side view of the distal end of the deployment assembly of FIG. 11A, according to one embodiment.
Figure 12A:
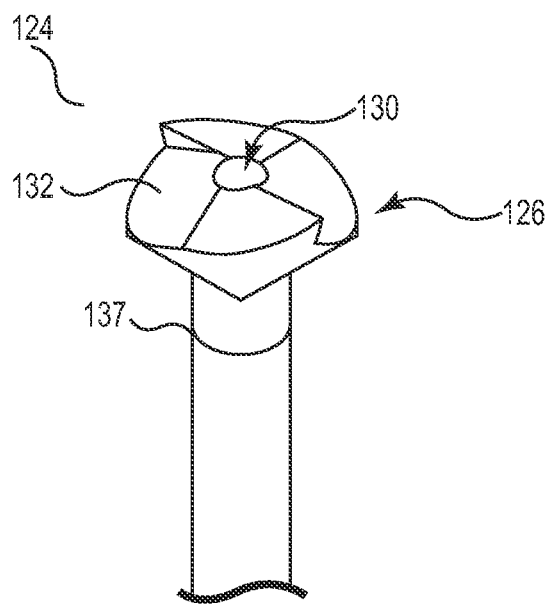
FIG. 12A is a perspective view of a distal end of a deployment tube, according to one embodiment.
Figure 12B:
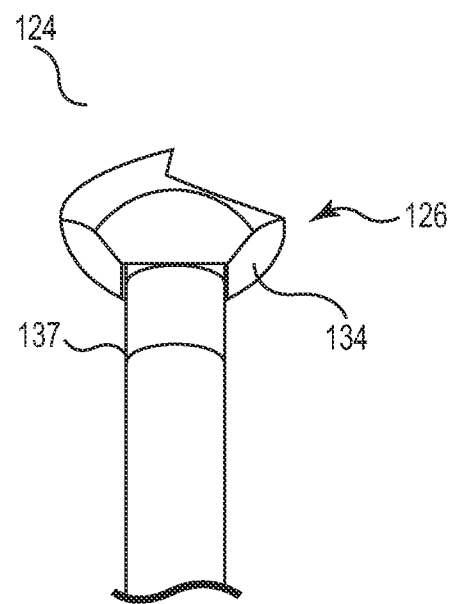
FIG. 12B is another perspective view of the distal end of the deployment tube of FIG. 12A, according to one embodiment.

Next, the treatment device is implanted. In one embodiment, both a first anchor and tether component are implanted first. The implantation can be accomplished according to one implementation using an implantation assembly 120 (also referred to as a "deployment assembly") as best shown in FIGS. 11A, 11B, and 11C. FIG. 11C is an expanded cross-sectional view of the distal end of the assembly 120 as shown in FIGS. 11A and 11B. This particular assembly embodiment 120 has an outer tube 122 with a deployment tube 124 and a tether 136 disposed within the outer tube 122 and a pre-deployment first anchor 144 disposed at the distal end of the outer tube 122. FIGS. 12A and 12B also depict the distal end of the deployment tube 124. As shown in those figures, the deployment tube 124 has a deployment anvil 126 at the distal end, a deployment grip 128 at the proximal end, a separation point 137 proximal to the anvil 126, and a lumen 130 disposed throughout the length of the tube 124. The separation point 137, according to one embodiment, is a portion of the deployment tube 124 having a smaller circumference than the rest of the tube 124, thereby creating a weaker point along the tube 124 that can be used to separate the tube 124 portion proximal to the separation point 137 from the anvil 126 as will be described in detail below. Alternatively, the separation point 137 can be any known configuration or component along the tube 124 that can create a weaker point that allows for separation of part of the tube 124.

The deployment tube 124 is moveable longitudinally in relation to the outer tube 122. The anvil 126 has a distal face 132 that, according to one embodiment, is circular and fluted as best shown in FIG. 12A. Alternatively, the distal face 132 can have any sort of shape or configuration that allows the distal face 132 to be used to drill into bone. The anvil 126 also has a proximal face 134 that, in one implementation, has a relatively square tapering configuration as best shown in FIG. 12B. In a further embodiment, the anvil 126 can be any component or structure of any configuration disposed at the distal end of the deployment tube 124 that can be used to help deploy the anchor prongs as described below.

The assembly 120 also contains a tether 136 disposed within the outer tube 122 and over the deployment tube 124. In one embodiment, the tether 136 can be identical to or similar to the tether 16 depicted in FIG. 2 and described above. The tether 136 has a flexible component 136A and a base component 136B, with the base component 136B having a threaded portion 138 and a non-threaded portion 140. The flexible component 136A in this embodiment comprises sutures 136A that are tied to the base component 136B at the holes 142 in the base component 136B.

Figure 13A:
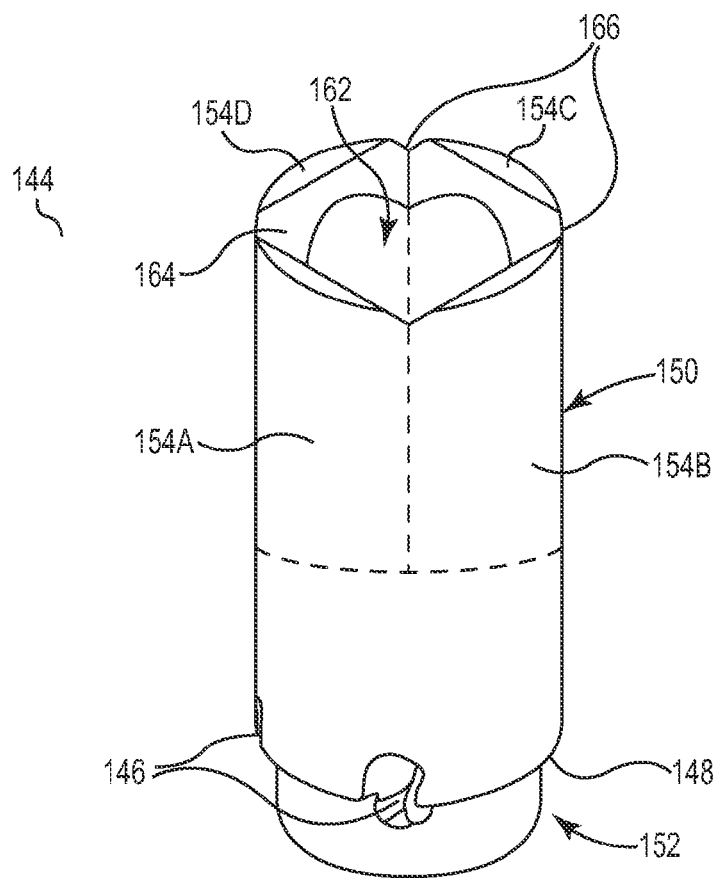
FIG. 13A is a perspective view of a pre-deployment anchor, according to one embodiment.
Figure 13B:
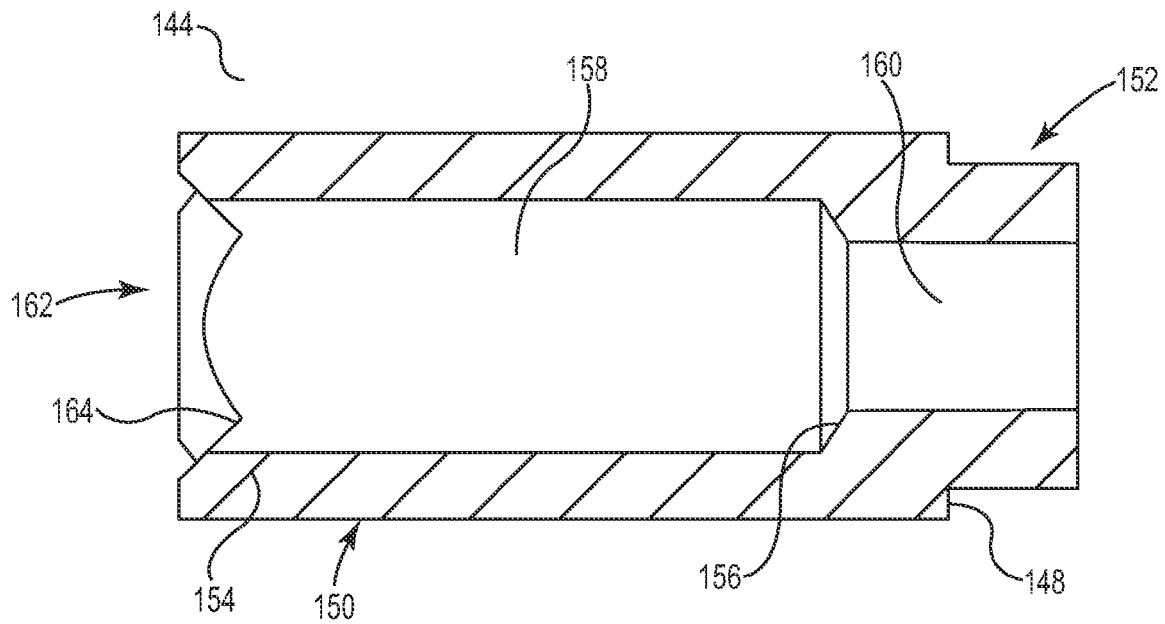
FIG. 13B is a cross-sectional side view of the pre-deployment anchor of FIG. 13A, according to one embodiment.

Disposed at the distal end of the assembly 120 (but proximal to the deployment anvil 126) is a pre-deployment first anchor 144 having holes 146 defined in the proximal end of the pre-deployed anchor 144. Two additional depictions of the pre-deployment first anchor 144 are provided in FIGS. 13A and 13B, showing the pre-deployment anchor 144 prior to deployment of the prongs 154A, 154B. In accordance with one implementation, the pre-deployed first anchor 144 can—upon deployment—be identical to or similar to the first anchor 12 depicted in FIG. 2 and described above. The pre-deployment first anchor 144 has an outer shoulder 148 disposed between a large portion 150 and a small portion 152. As shown by the dotted lines, four pre-deployment prongs 154A, 154B, 154C, 154D similar to those shown in FIG. 2 form the distal portion of the large portion 150 as shown by the dotted lines. This distal portion is reconfigured into deployed prongs using a process described in detail below.

As mentioned above, the small portion 152 of the anchor 144 has a diameter that is smaller than the large portion 150. In the assembly 120 as best shown in FIG. 11C, the distal end of the outer tube 122 is disposed over the small portion 152 of the pre-deployed anchor 144 and contacts the shoulder 148. In one embodiment, the outer tube 122 has tabs 145 that are positioned into the anchor 144 where the outer tube 122 is positioned over the small portion 152 as best shown in FIG. 11A. The tabs 145 can rotationally couple the outer tube 122 and the anchor 144 such that the anchor 144 is rotated when the outer tube 122 is rotated. In addition, the pre-deployment configuration of the first anchor 144 has an inner shoulder 156 (as best shown in FIG. 13B) that defines a transition between a first lumen 158 and a second lumen 160 having a smaller diameter than the first lumen 158. Further, the pre-deployment anchor 144 has a distal opening 162 that includes a beveled configuration 164 that defines a square shape at the opening 162 with notches 166 in each corner of the square shaped bevel configuration 164. In one embodiment, the beveled configuration 164 is configured to receive the proximal face 134 of the anvil 126 as will be described in further detail below. That is, the generally square-shaped proximal face 134 is positioned or seated into the beveled configuration 164 at the distal opening 162 of the pre-deployment configuration of the anchor 144. Alternatively, the proximal face 134 and the beveled configuration 164 can both have any shape that allows for the seating of the face 134 in the beveled configuration while also providing for the deployment of the prongs 154A, 154B as described in detail below.

Figure 14:
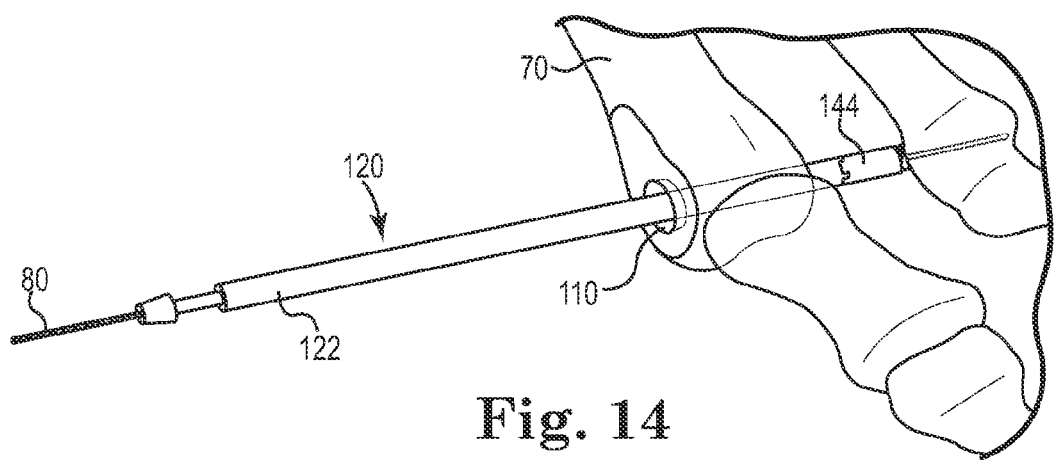
FIG. 14 is a schematic depiction of the foot of FIG. 10, in which a deployment assembly has been positioned over the guide wire, according to one embodiment.
Figure 15:
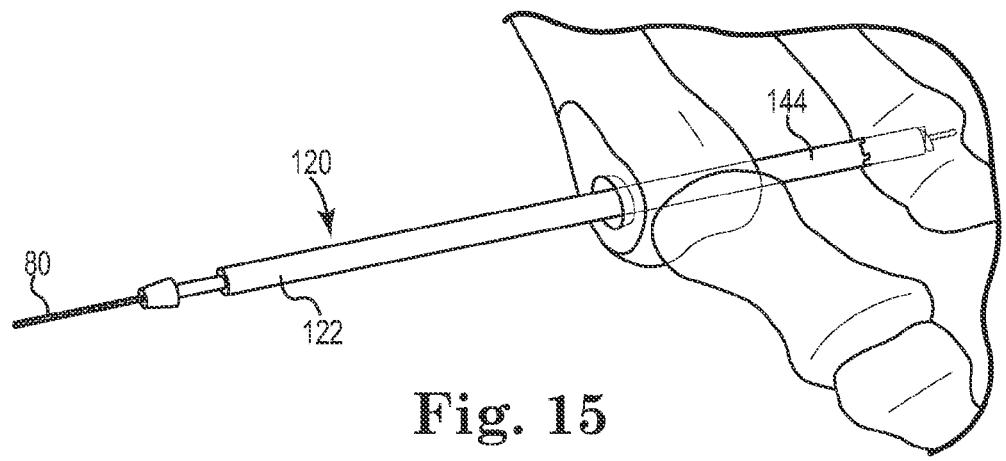
FIG. 15 is a schematic depiction of the foot of FIG. 14, in which the distal end of the deployment assembly has been positioned into the second metatarsal bone, according to one embodiment.

In use, the implantation assembly 120 can be used to implant the first anchor 144 into the second metatarsal and then deploy the prongs 154 on the anchor 144. FIG. 14 depicts one embodiment of the implantation assembly 120 being positioned over the guide wire 80 and moved distally through the lumen or hole 110 in the first metatarsal bone 70 and into contact with the second metatarsal bone 74. In the next step as shown in FIG. 15, the first anchor 144 is positioned in the second metatarsal 74. In one embodiment, the anchor 144 is positioned by manually "drilling" the entire assembly 120 (manually rotating the assembly 120 while urging the assembly 120 in a distal direction into the second metatarsal bone 74) using the fluted distal face 132 of the anvil 126. Alternatively, the anchor 144 can be positioned in the second metatarsal bone 74 by coupling a proximal portion of the assembly 120 to a power drill and using the power drill to urge the fluted distal face 132 against and into the bone 74 and thereby position the anchor 144 as shown in FIG. 15. In a further alternative, fluoroscopy may be used to facilitate the depth of positioning of the anchor 144 into the second metatarsal 74.

Figure 16:
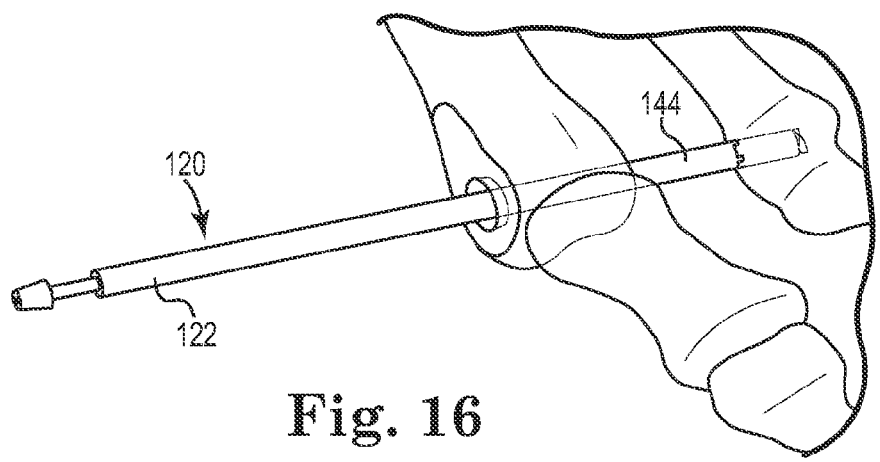
FIG. 16 is a schematic depiction of the foot of FIG. 15, in which the guide wire has been removed, according to one embodiment.

As shown in FIG. 16, once the anchor 144 is positioned, the guide wire can be removed.

Figure 17A:
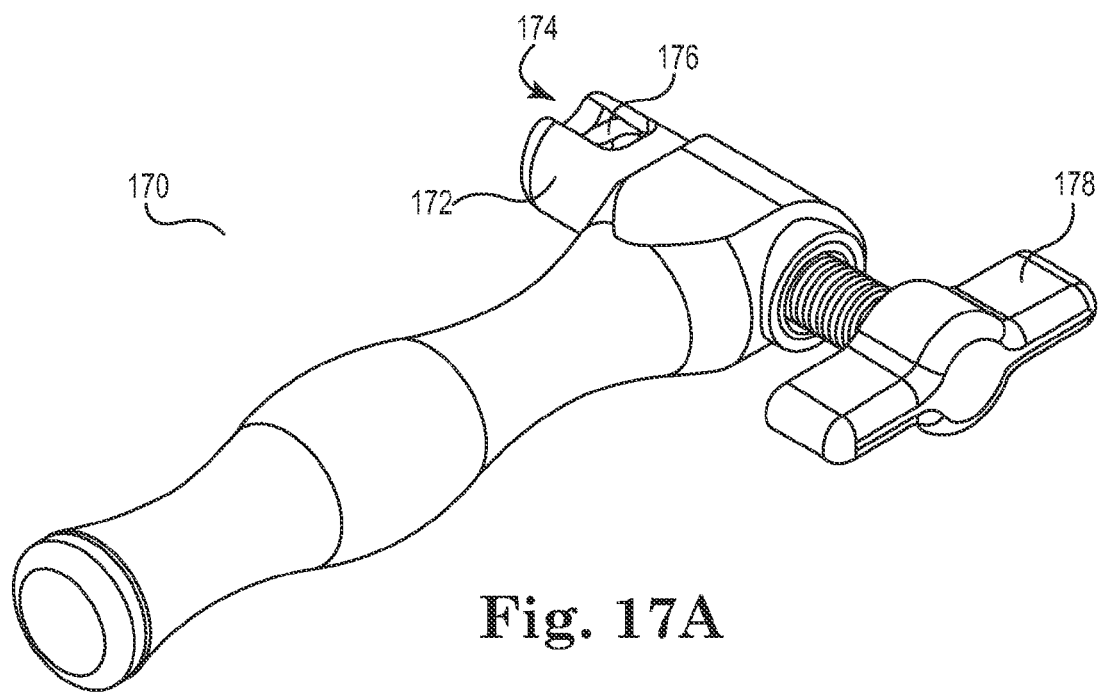
FIG. 17A is a perspective view of a deployment tool, according to one embodiment.
Figure 17B:
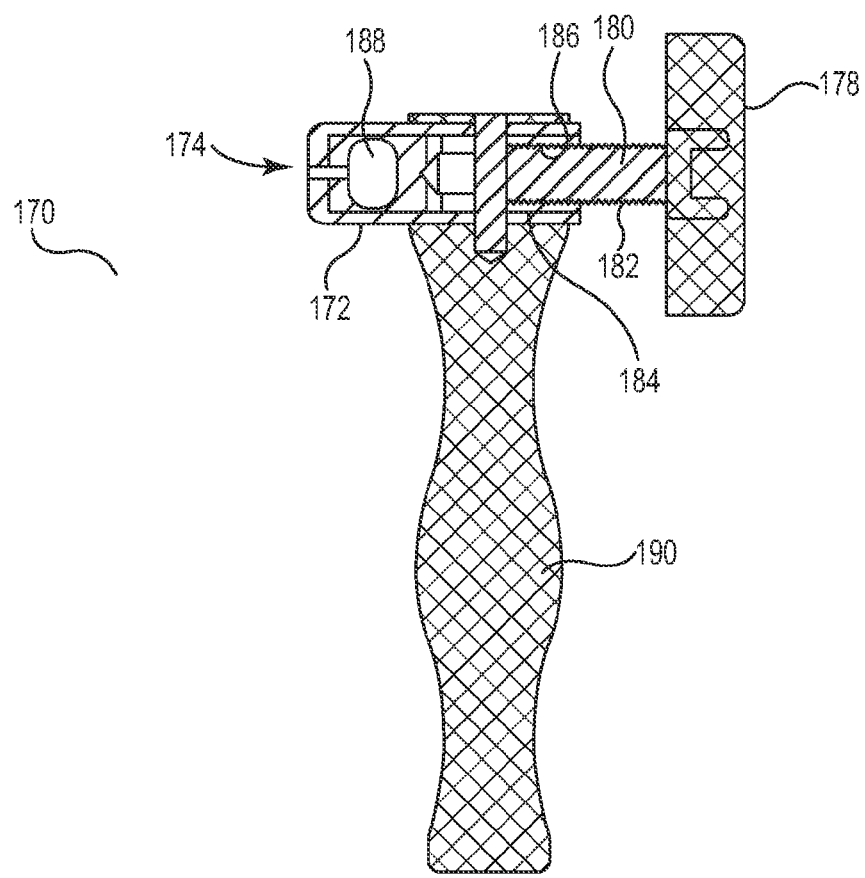
FIG. 17B is a cross-sectional side view of the deployment tool of FIG. 17A, according to one embodiment.

Next, the first anchor 144 is deployed within the second metatarsal bone 74. In one embodiment, the deployment is accomplished using a deployment tool 170 such as that shown in FIGS. 17A and 17B, which moves anvil 126 proximally relative to the first anchor 144 and deploys the prongs 154 in a "rivet-like" or "peeling" manner into the cancellous bone. Alternatively, any known method or device for deploying the anchor 144 can be used. The deployment tool 170 has an external body 172 having an opening 174 defined on the distal end of the external body 172 and a receiving slot 176 defined along a side of the external body 172 that is in communication with the opening 174. As best shown in FIG. 17B, in one implementation, the external body 172 has a moveable internal body 184 disposed within the external body 172. The internal body 184 defines a receiving cavity 188 and is moveable in relation to the external body 172 and the handle 190, which can be used by a user such as a surgeon to grasp and hold the tool 170. A deployment knob 178 having a shaft 180 is coupled to the tool 170, with the shaft 180 disposed within a lumen 186 of the internal body 184. The shaft 180 has threads 182 that engage with threads on the lumen 186, such that rotation of the knob 178 rotates the threads 182 which causes the internal body 184 to move toward or away from the knob 178.

Figure 18:
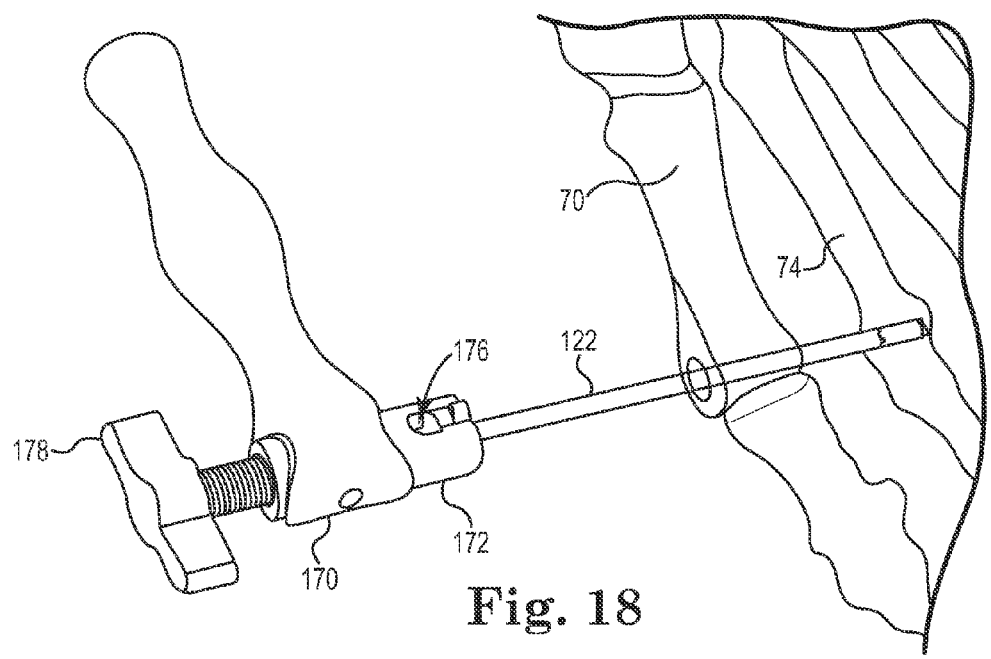
FIG. 18 is a schematic depiction of the foot of FIG. 16, in which a deployment tool has been coupled to the deployment assembly, according to one embodiment.

In use, as shown in FIG. 18 in accordance with one embodiment, the tool 170 is coupled to the proximal end of the assembly 120 that is already positioned through the first metatarsal bone 70 and into the second metatarsal bone 74 as shown. More specifically, the tool body 172 is positioned with respect to the assembly 120 such that the deployment grip 128 is inserted through the receiving slot 176 and positioned in the receiving cavity 188 (best shown in FIG. 17B). Once the grip 128 is positioned appropriately, the user can turn the knob 178. When the knob 178 is turned, the internal body 184 as best shown in FIG. 17B is urged toward the knob 178, thereby pulling the deployment grip 128 proximally. As the deployment grip 128 is moved proximally, the outer tube 122 remains stationary in relation to the grip 128 because the proximal end of the outer tube 122 is in contact with the distal end of the external body 172.

In one embodiment, the movement of the deployment grip 128 in a proximal direction moves the entire deployment tube 124 in a proximal direction relative to the outer tube 122, thereby urging the deployment anvil 126 proximally against the first anchor 144. That is, the deployment tool 170 creates a differential force between the outer tube 122 and the deployment tube 124. As the anvil 126 is urged against the pre-deployment configuration of the anchor 144, the proximal face 134 of the anvil 126 is urged against the beveled configuration 164 of the anchor 144. Alternatively, it could be viewed that the deployment tube 124 and the anvil 126 remain relatively stationary and the outer tube and first anchor 144 move distally. Either way, the movement of the anvil 126 and anchor 144 relative to one another results in the deployment of the prongs 154.

Figure 19:
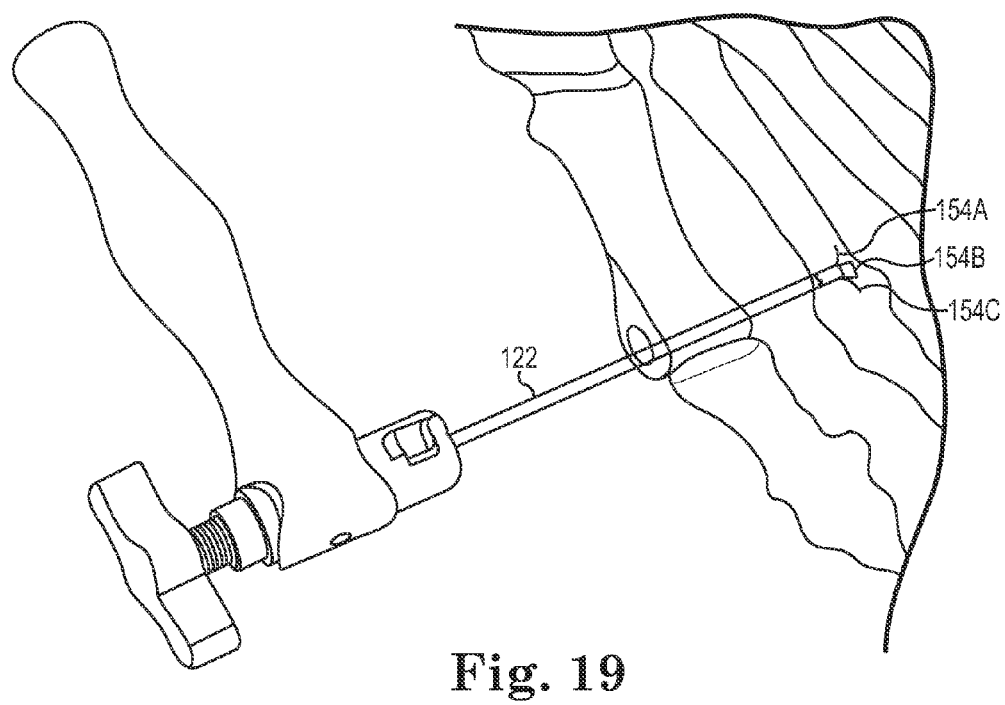
FIG. 19 is a schematic depiction of the foot of FIG. 18, in which the prongs on the first anchor have been deployed, according to one embodiment.

In this embodiment, the pre-deployment configuration of the anchor 144 is configured to ultimately deform or be urged into the deployed configuration as best shown in FIG. 19 as a result of the proximal movement of the anvil 126. More specifically, in the embodiment depicted in FIGS. 11A, 11B, 11C, 12A, 12B, 13A, and 13B, the beveled configuration 164 with the notches 166 is configured to allow for deformation of the large portion 150 such that the prongs 154 are deployed as best shown in FIG. 19. Even more specifically, the notches 166 at the opening 162 provide weak points at the distal end of the large portion 150 such that when the anvil 126 is urged proximally against the distal end of the pre-deployment configuration of the anchor 144, the large portion 150 separates at each of the notches, thereby forming the deployed prongs 154A, 154B, 154C (154D is not visible in this figure) as best shown in FIG. 19 along the dotted lines depicted in FIG. 13A. Alternatively, the pre-deployment configuration of the anchor 144 can have any structure that allows for proximal movement of an anvil-like structure causing prongs to be deployed. The anvil 126 can be urged proximally until it encounters the inner shoulder 156 of the anchor 144, at which point it cannot move further proximally in relation to the anchor 144. Once the anvil 126 contacts the inner shoulder 156, continued urging of the deployment tube 124 in the proximal direction causes the deployment tube 124 to fracture at the separation point 137 as best shown in FIGS. 12A and 12B, thereby separating the portion of the tube 124 proximal to the separation point 137 and allowing the user to remove that proximal portion of the tube 124 by moving the proximal portion proximally until it is removed from outer tube 122 of the assembly 120. Alternatively, the deployment tube 124 can be removed by any known mechanism or method. The outer tube 122 is then removed as well. Alternatively, the outer tube 122 can be removed prior to the removal of the deployment tube 124.

Figure 20:
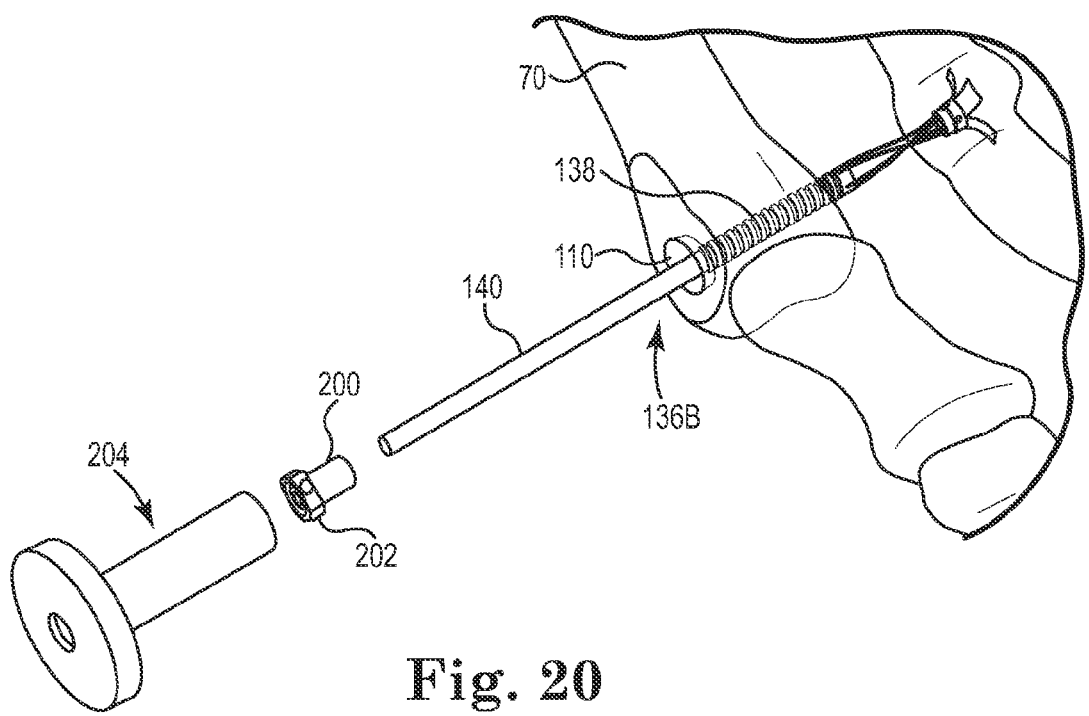
FIG. 20 is a schematic depiction of the foot of FIG. 19, in which the deployment tool, outer tube, and deployment tube have been removed and a second anchor and anchor placement tool are being positioned to be inserted over the base component of the tether, according to one embodiment.

Once the deployment tube 124 and outer tube 122 have been removed, a second anchor 200 is coupled to the base component 136B, as shown according to one embodiment in FIG. 20. It is understood that the second anchor 200 can be identical or similar to the second anchor 14 depicted in FIGS. 2, 4A, and 4B. Alternatively, the second anchor 200 can be any known anchor that can be coupled to the proximal end of the treatment device as described herein for purposes of fixing the proximal end of the device to the first metatarsal bone.

Figure 21A:
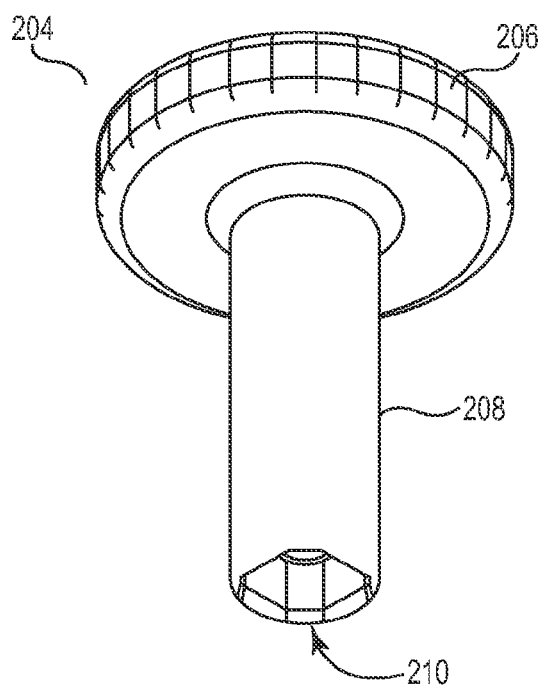
FIG. 21A is a perspective view of an anchor placement tool, according to one embodiment.
Figure 21B:
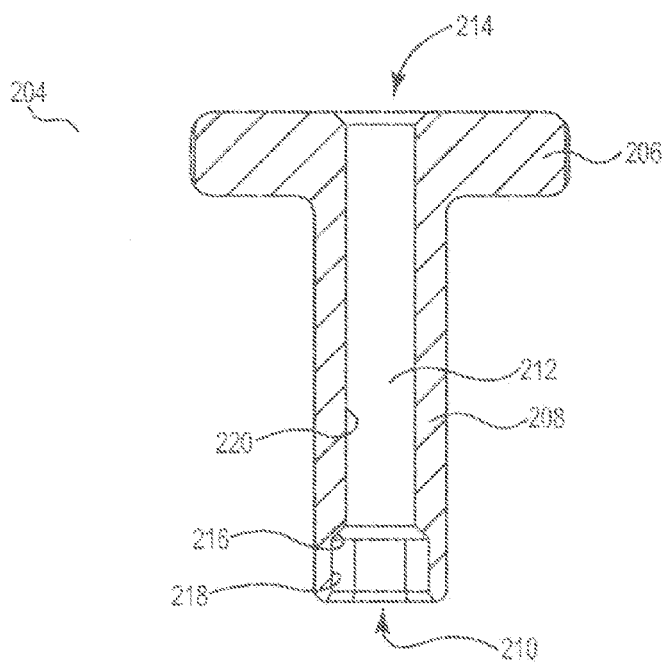
FIG. 21B is a cross-sectional side view of the anchor placement tool of FIG. 21A, according to one embodiment.

In this embodiment, an anchor placement tool 204 is used to assist with coupling the anchor 200 to the base component 136B. One version of the placement tool 204 is shown in further detail in FIGS. 21A and 21B. Alternatively, any known tool that could be used to assist with coupling the anchor 200 to the base component 136B can be used. The placement tool 204 as shown has a knob 206, a shaft 208, and a distal opening 210. Further, the tool 204 has a lumen 212 disposed throughout the length of the tool 204 as shown, with the lumen 212 being in fluid communication with the opening 210 in the distal end and an opening 214 in the proximal end. In the lumen, a shoulder 216 separates a distal lumen portion 218 adjacent to the opening 210 that is larger than the proximal lumen portion 220. As best shown in FIG. 21A, the opening 210 and distal lumen portion 218 has a square configuration. The opening 210 and distal lumen portion 218 are configured to receive an anchor. In one embodiment, the square configuration of the opening 210 and distal lumen portion 218 engages with a square head of the anchor (such as anchor 200, for example) such that the tool 204 can be used to rotate the anchor.

Returning to FIG. 20, in use, the anchor placement tool 204 is positioned with respect to the second anchor 200 such that the head 202 of the second anchor 200 is positioned within the opening 210 of the tool 204. The tool 204 and anchor 200 are then urged distally over the base component 136B. More specifically, the tool 204 and anchor 200 are urged distally over the non-threaded portion 140 of the base component 136B until the anchor 200 reaches the threaded portion 138. Once the anchor 200 reaches this position, it is urged distally onto the threaded portion by rotating the tool 204 and thereby rotating the anchor 200, which causes the threads (not shown) on the inner lumen of the anchor 200 to engage with the threads on the threaded portion 138 and advance the anchor 200 distally over the threaded portion 138. As the anchor 200 moves distally over the threaded portion 138, the anchor is positioned in the lumen 110 of the first metatarsal 70 and the anchor head 202 is positioned in the counterbore 112.

It is understood that the rotating of the anchor 200 on the threaded portion 138 of the base component 136B allows the user to vary the length of the tether 136 between the first and second anchors 144, 200. More specifically, the user can shorten the length of the tether 136 between the two anchors 144, 200 to a desired length by advancing the anchor 200 further distally along the threaded portion 138. Alternatively, the user can increase the length of the tether 136 by moving the anchor 200 proximally along the threaded portion 138. As such, the user can control the amount of tension applied to the first and second metatarsals 70, 74 based on the length of the tether 136, which thereby can adjustably change the inter metatarsal angle between the first and second metatarsal bones.

Like the adjustability described above, other alternative embodiments of the treatment device contemplated herein include a tether 136 that allows for controllable or adjustable dynamic tension or tightening. More specifically, the tether 136 can be configured to apply a dynamic tightening or dynamic tension force that urges the first and second metatarsal bones together based on the concepts originally disclosed in U.S. application Ser. No. 12/371,354, which was incorporated by reference above. As described in detail in that application, these dynamic tightening or tension implementations can provide a slow correction of the joint deformity by decreasing the metatarsal angle over time.

Once the anchor 200 is positioned in the first metatarsal 70, the non-threaded portion 140 (and any portion of the threaded portion 138 that extends or projects proximally beyond the anchor 200) is removed. In one embodiment, those portions are removed by cutting the base component 136B with a cutting tool at the anchor 200. Alternatively, any known method or mechanism can be used to remove those portions extending proximally beyond the anchor.

In one alternative embodiment, a further step can be performed at this point to further enhance the hallux valgus treatment. More specifically, the medial MTP capsule tissue, which was necessarily cut and laid back for purposes of the implantation procedure as described above, can be closed and "tightened" using the bone anchor 200 and some additional sutures. In one embodiment, the use of the sutures and the anchor 200 to tighten the capsule tissue is described in detail in U.S. application Ser. No. 12/691,646, which was incorporated by reference above. The tightening or foreshortening of the medial tissue can cause the first toe to be aligned more straightly with the first metatarsal bone, thereby supplementing the treatment provided by the implanted device 230.

Figure 22:
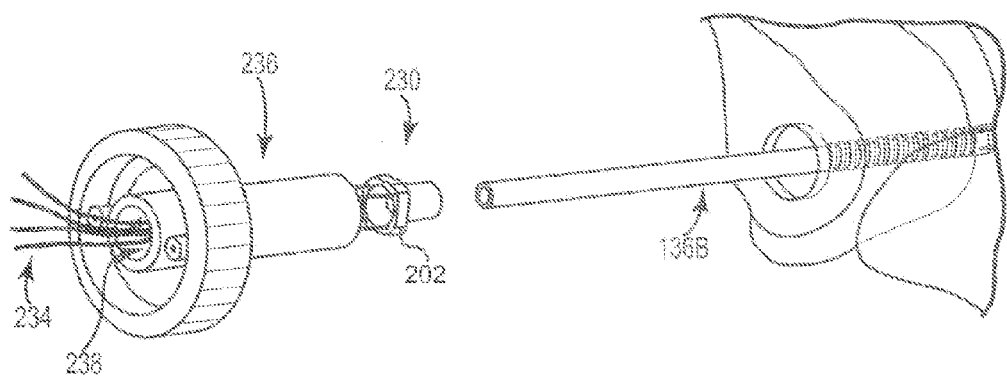
FIG. 22 is a schematic depiction of the foot of FIG. 19, in which the deployment tool, outer tube, and deployment tube have been removed and alternative embodiments of a second anchor and an anchor placement tool are being positioned to be inserted over the base component of the tether, according to one embodiment.

According to one implementation in which the MTP capsule tissue is tightened as described above, an alternative second bone anchor 230 embodiment is provided with the sutures 234 pre-positioned on the anchor 230 as shown in FIG. 22. More specifically, the second bone anchor 230 has a head 202 having sutures 234 attached thereto prior to coupling the anchor 230 to the tether base component 136B. That is, the sutures 234 are "pre-loaded" onto the anchor 230. In one embodiment as shown, for purposes of implantation, the sutures 234 extending from the anchor 230 are positioned through the lumen 238 in the driver 236 such that the sutures 234 extend from the proximal end of the driver 236. The remaining steps of the procedure can proceed as described above, and then the sutures 234 can be used in a MTP capsule tissue tightening procedure as described above.

Figure 23:
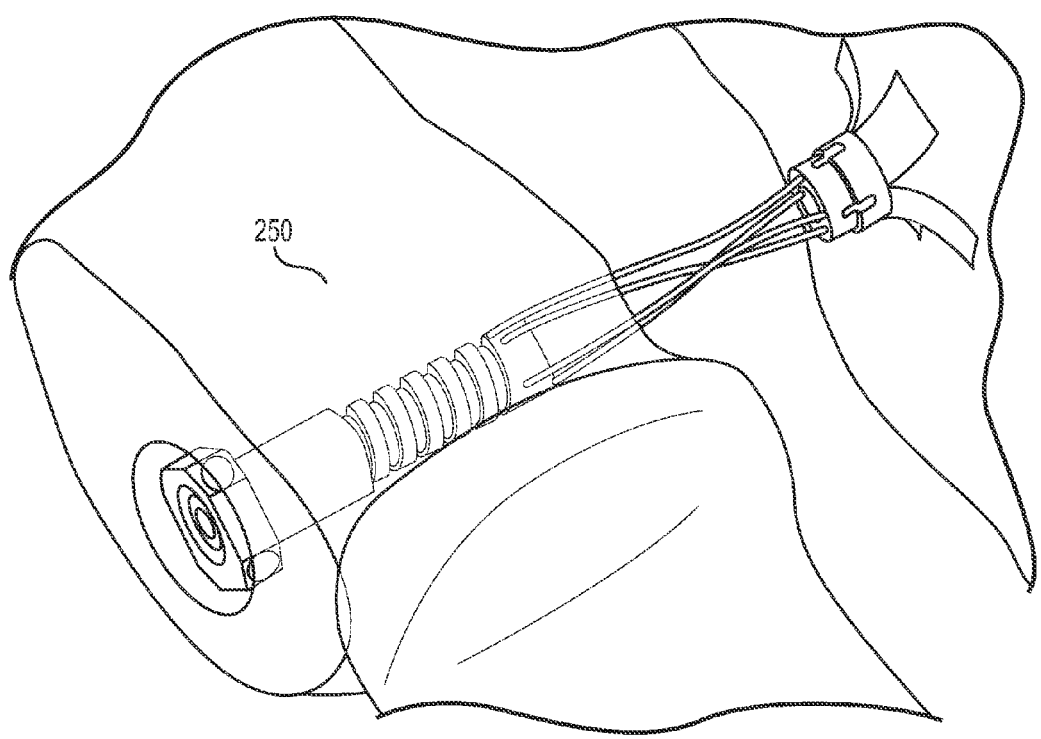
FIG. 23 is a schematic depiction of an implantable bone deformity treatment device implanted in a patient's foot, according to one embodiment.

Once the excess length of the base component 136B is removed (and, in some embodiments, the capsule tissue is tightened using sutures), the treatment device 250 is fully implanted according to one embodiment as shown in FIG. 23.

Although the present invention has been described with reference to preferred embodiments, persons skilled in the art will recognize that changes may be made in form and detail without departing from the spirit and scope of the invention.

What is claimed is:

1. A bone anchor assembly, comprising:
a distal body, said distal body having a lumen disposed throughout a length of said distal body and having a distal opening defined in a distal end of said distal body and in communication with said lumen and a proximal opening defined in a proximal end of said distal body and in communication with said lumen;
an anvil disposed at a distal end of said distal body, said anvil having a transverse dimension larger than said lumen, said anvil connected to an elongated pull-member located within said lumen and extending an entire length of said lumen;
a tether comprising a flexible component and a tether base component, said flexible component being connected at a first end to said distal body and being connected at a second end to said tether base component;
an outer tube surrounding said tether and bearing against a feature of said distal body,
wherein, upon retraction of said anvil in a proximal direction, at least some of said distal body is able to be reconfigured to a deployed configuration comprising at least two prongs extending away from the distal body.

2. The assembly of claim 1, wherein said distal body comprises a large portion and a small portion and a shoulder disposed where said large portion and said small portion meet each other.

3. The assembly of claim 2, wherein said outer tube surrounding said tether bears against said shoulder of said distal body.

4. The assembly of claim 1, wherein said tether base component has external threads on a threaded portion.

5. The assembly of claim 4, further comprising a head having a lumen having internal threads that are mateable with said external threads on said tether base component.

6. The assembly of claim 4, wherein said external threads on said tether base component are suitable to engage with an anchor.

7. The assembly of claim 6, wherein said distal body is suitable to anchor in a first bone and said anchor is suitable to bear against a second bone.

8. The assembly of claim 7, wherein said first bone is a second metatarsal and said second bone is a first metatarsal.

9. The assembly of claim 1, wherein said distal body has four notches.

10. The assembly of claim 1, wherein said anvil has sharp corners and wherein said distal body has notches, and wherein said sharp corners correspond to said notches.

11. The assembly of claim 1, wherein said tether base component has holes to receive said flexible component.

12. The assembly of claim 1, wherein said distal body has holes to receive said flexible component.

13. The assembly of claim 1, wherein said distal body comprises a deployment section proximal to the distal end of the distal body, the deployment section having a pre-deployment cylindrical configuration and a deployment configuration comprising at least two prongs extending away from the distal body when said anvil is moved proximally relative to said distal boxy.

14. The assembly of claim 1, wherein said distal body is capable of separating into four prongs.

15. The assembly of claim 1, wherein said at least two prongs are configured to be 2 to 10 millimeters away from a proximal surface of said distal body.

16. The assembly of claim 1, wherein said anvil is centrally located with respect to said distal body.

17. The assembly of claim 1, wherein said anvil has a distal face that is circular and fluted suitable to drill into bone.

18. The assembly of claim 1, wherein said anvil has a proximal face that either is conical or is tapering on four sides.

19. The assembly of claim 1, wherein said elongated pull-member comprises a separation point suitable for promoting fracturing said elongated pull-member from said anvil upon application of suitable force.

20. The assembly of claim 19, wherein said pull-member and said anvil are hollow having a lumen lengthwise therethrough.

21. The assembly of claim 1, wherein said distal body has tabs at an interface with said outer tube, said tabs being suitable to prevent relative rotation between said distal body and said outer tube.

22. The assembly of claim 1, wherein said assembly has a central axis each component of said assembly that is located on said axis has a central hole therethrough suitable to accept a guidewire.

23. A bone anchor comprising:
a distal body, said distal body having a lumen disposed throughout a length of said distal body and having a distal opening defined in a distal end of said distal body and in communication with said lumen and a proximal opening defined in a proximal end of said distal body and in communication with said lumen;
an anvil disposed at a distal end of said distal body, said anvil having a transverse dimension larger than said lumen, said anvil connected to an elongated pull-member located within said lumen and extending an entire length of said lumen;
wherein said elongated pull-member and said anvil have an axial hole extending an entire length of said elongated pull-member and through said anvil,
wherein said elongated pull-member comprises a separation point suitable for promoting fracturing said pull-member from said anvil upon application of suitable force,
further comprising a guidewire extending through said elongated pull-member and through said anvil.

24. The bone anchor of claim 23, wherein a distal end of said anvil is circular and fluted.

25. The bone anchor of claim 23, wherein, upon retraction of said anvil in a proximal direction, at least some of said distal body is able to be reconfigured to a deployed configuration comprising at least two prongs extending away from said body.

* * * * *